(12) United States Patent
Facchetti et al.

(10) Patent No.: US 7,893,265 B2
(45) Date of Patent: Feb. 22, 2011

(54) METHODS FOR PREPARING ARENE-BIS (DICARBOXIMIDE)-BASED SEMICONDUCTING MATERIALS AND RELATED INTERMEDIATES FOR PREPARING SAME

(75) Inventors: Antonio Facchetti, Chicago, IL (US); Tobin J. Marks, Evanston, IL (US); He Yan, Skokie, IL (US)

(73) Assignee: Polyera Corporation, Skokie, IL (US)

( * ) Notice: Subject to any disclaimer, the term of this patent is extended or adjusted under 35 U.S.C. 154(b) by 610 days.

(21) Appl. No.: 12/006,934

(22) Filed: Jan. 7, 2008

(65) Prior Publication Data
US 2008/0177073 A1 Jul. 24, 2008

Related U.S. Application Data

(60) Provisional application No. 60/879,145, filed on Jan. 8, 2007.

(51) Int. Cl.
*C07D 471/02* (2006.01)
*C07D 493/02* (2006.01)

(52) U.S. Cl. .................... 546/37; 549/232; 549/234; 546/66; 548/418

(58) Field of Classification Search .................. 546/37, 546/66; 548/418; 549/232, 234
See application file for complete search history.

(56) References Cited

U.S. PATENT DOCUMENTS

| | | | |
|---|---|---|---|
| 2,087,133 A | 7/1937 | Vollmann | |
| 4,378,302 A | 3/1983 | Aftergut et al. | |
| 4,611,385 A | 9/1986 | Forrest et al. .................. 29/574 |
| 4,846,892 A | 7/1989 | Henning et al. | |
| 5,405,962 A | 4/1995 | Muellen et al. | |
| 5,472,494 A | 12/1995 | Hetzenegger et al. | |
| 5,539,100 A | 7/1996 | Wasielewski et al. | |
| 5,677,417 A | 10/1997 | Muellen et al. | |
| 5,808,073 A | 9/1998 | Böhm et al. | |
| 5,908,583 A | 6/1999 | Havinga et al. | |
| 5,986,099 A | 11/1999 | Müllen et al. | |
| 6,063,181 A | 5/2000 | Bohm et al. | |
| 6,084,099 A | 7/2000 | Hackmann et al. | |
| 6,099,636 A | 8/2000 | Henning et al. | |
| 6,124,458 A | 9/2000 | Müellen et al. | |
| 6,143,905 A | 11/2000 | Bohm et al. | |
| 6,165,661 A | 12/2000 | Hsiao et al. | |
| 6,184,378 B1 | 2/2001 | Bohm et al. | |
| 6,252,245 B1 | 6/2001 | Katz et al. | |
| 6,287,738 B1 | 9/2001 | Duff et al. | |
| 6,326,494 B1 | 12/2001 | Bohm et al. | |
| 6,348,595 B1 | 2/2002 | Hendi | |
| 6,486,319 B1 | 11/2002 | Böhm et al. | |
| 6,533,857 B1 | 3/2003 | Schmid et al. | |
| 6,551,717 B2 | 4/2003 | Katz et al. .................. 428/447 |
| 6,585,914 B2 | 7/2003 | Marks et al. | |
| 6,608,323 B2 | 8/2003 | Marks et al. | |
| 6,656,651 B1 | 12/2003 | Bender et al. | |
| 6,727,318 B1 | 4/2004 | Mathauer et al. | |
| 6,784,301 B2 | 8/2004 | Hackmann et al. | |
| 6,806,368 B2 | 10/2004 | Wurthner et al. | |
| 6,878,825 B2 | 4/2005 | Krieger et al. | |
| 6,890,377 B2 | 5/2005 | Böhm et al. | |
| 6,916,928 B2 | 7/2005 | Becker et al. | |
| 6,986,811 B2 | 1/2006 | Könemann et al. | |
| 7,083,675 B2 | 8/2006 | Mizuguchi et al. | |
| 7,105,046 B2 | 9/2006 | Mizuguchi et al. | |
| 7,105,674 B2 | 9/2006 | Hackmann et al. | |
| 7,326,956 B2 | 2/2008 | Shukla et al. | |
| 7,422,777 B2 | 9/2008 | Shukla et al. | |
| 7,671,202 B2 * | 3/2010 | Marks et al. .................. 546/37 |
| 2003/0181721 A1 | 9/2003 | Wurthner et al. | |
| 2003/0219625 A1 | 11/2003 | Wolk et al. | |
| 2004/0013959 A1 | 1/2004 | Bender et al. | |

(Continued)

FOREIGN PATENT DOCUMENTS

DE  2951349 A1  7/1981

(Continued)

OTHER PUBLICATIONS

Ahrens et al., "Cyanated Perylene-3,4-dicarboximides and Perylene-3,4:9,10-bis(dicarboximide):Facile Chromophoric Oxidants for Organic Photonics and Electronics," *Chem. Mater.*, 15:2684-2686 (2003).

(Continued)

*Primary Examiner*—Charanjit S Aulakh
(74) *Attorney, Agent, or Firm*—K&L Gates LLP

(57) ABSTRACT

The present teachings provide compounds of formulae I and II:

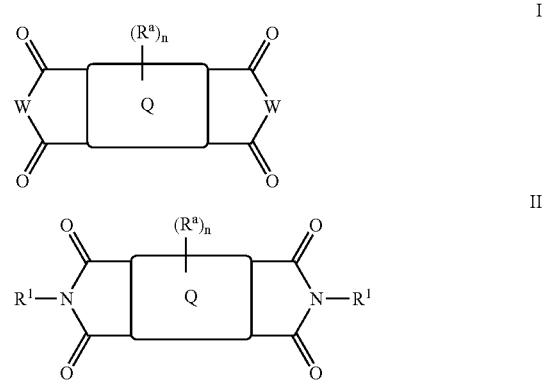

where Q, $R^a$, $R^1$, W, and n are as defined herein. The present teachings also provide methods of preparing compounds of formulae I and II, including methods of preparing compounds of formula II from compounds of formula I. The compounds disclosed herein can be used to prepare semiconductor materials and related composites and electronic devices.

19 Claims, 10 Drawing Sheets

U.S. PATENT DOCUMENTS

| | | |
|---|---|---|
| 2004/0023061 A1 | 2/2004 | Kathirgamanathan et al. |
| 2005/0075453 A1 | 4/2005 | Mathauer et al. |
| 2005/0092982 A1 | 5/2005 | Mullen et al. |
| 2005/0106415 A1 | 5/2005 | Jarikov et al. |
| 2005/0131220 A1 | 6/2005 | Dung et al. |
| 2005/0171252 A1 | 8/2005 | Schambony et al. |
| 2005/0176970 A1 | 8/2005 | Marks et al. |
| 2005/0222416 A1 | 10/2005 | Bohm et al. |
| 2005/0238974 A1 | 10/2005 | Sekiya et al. |
| 2005/0251930 A1 | 11/2005 | Erk et al. |
| 2006/0058330 A1 | 3/2006 | Krieger et al. |
| 2006/0075585 A1 | 4/2006 | Krieger et al. |
| 2006/0131564 A1 | 6/2006 | Shukla et al. |
| 2006/0134823 A1 | 6/2006 | Shukla et al. |
| 2006/0141287 A1 | 6/2006 | Klubek et al. |
| 2006/0210898 A1 | 9/2006 | Jubran |
| 2006/0229385 A1 | 10/2006 | Boehm |
| 2006/0237712 A1 | 10/2006 | Shukla et al. |
| 2007/0026332 A1 | 2/2007 | Ferrar et al. |
| 2007/0096084 A1 | 5/2007 | Shukla et al. |
| 2007/0116895 A1 | 5/2007 | Shukla et al. |
| 2008/0021220 A1 | 1/2008 | Marks et al. |
| 2008/0135833 A1 | 6/2008 | Shukla et al. |
| 2008/0161569 A1 | 7/2008 | Dung et al. |
| 2008/0167435 A1 | 7/2008 | Marks et al. |
| 2008/0185555 A1 | 8/2008 | Facchetti et al. |
| 2008/0185577 A1 | 8/2008 | Facchetti et al. |
| 2008/0249309 A1 | 10/2008 | Facchetti et al. |

FOREIGN PATENT DOCUMENTS

| | | |
|---|---|---|
| DE | 3434059 A1 | 3/1985 |
| DE | 3620332 A1 | 12/1987 |
| DE | 3703131 | 8/1988 |
| DE | 4018830 | 12/1991 |
| DE | 4338784 | 5/1995 |
| DE | 4440242 | 5/1996 |
| DE | 19501737 A1 | 7/1996 |
| DE | 19547210 A1 | 6/1997 |
| DE | 19622673 A1 | 12/1997 |
| DE | 19651712 A1 | 6/1998 |
| DE | 19709008 A1 | 9/1998 |
| DE | 10038672 A1 | 5/2002 |
| DE | 10148172 A1 | 4/2003 |
| EP | 0031065 | 10/1983 |
| EP | 0 217 256 | 4/1987 |
| EP | 0 422 535 | 4/1991 |
| EP | 0 826 740 | 3/1998 |
| EP | 0 861 878 | 9/1998 |
| EP | 0 896 964 | 2/1999 |
| EP | 0 990 951 | 4/2000 |
| EP | 1 172 700 | 1/2002 |
| EP | 1 671 674 | 6/2006 |
| FR | 1 526 496 | 5/1968 |
| FR | 2 237 922 | 2/1975 |
| JP | 05-025174 | 2/1993 |
| JP | 05-027459 | 2/1993 |
| JP | 11-119455 | 4/1999 |
| JP | 2002-302674 | 10/2002 |
| JP | 2003-327587 | 11/2003 |
| JP | 2004-093801 | 3/2004 |
| JP | 2004-093802 | 3/2004 |
| JP | 2004-152815 | 5/2004 |
| JP | 2005-154409 | 6/2005 |
| JP | 2005-189765 | 7/2005 |
| JP | 2005-209887 | 8/2005 |
| JP | 2006-028027 | 2/2006 |
| WO | 90/01480 | 2/1990 |
| WO | 96/22332 | 7/1996 |
| WO | 97/22607 | 6/1997 |
| WO | 97/22608 | 6/1997 |
| WO | 97/26301 | 7/1997 |
| WO | 98/32799 | 7/1998 |
| WO | 98/32802 | 7/1998 |
| WO | 98/49164 | 11/1998 |
| WO | 00/69829 | 11/2000 |
| WO | 02/14414 | 2/2002 |
| WO | 03/091345 | 11/2003 |
| WO | 03/104232 | 12/2003 |
| WO | 2004/029028 | 4/2004 |
| WO | 2005/047265 | 5/2005 |
| WO | 2005/070894 | 8/2005 |
| WO | 2005/070895 | 8/2005 |
| WO | 2005/078023 | 8/2005 |
| WO | 2005/092901 | 10/2005 |
| WO | 2006/021307 | 3/2006 |
| WO | 2006/037539 | 4/2006 |
| WO | 2006/050860 | 5/2006 |
| WO | 2006/093965 | 9/2006 |
| WO | 2006/115714 | 11/2006 |
| WO | 2007/074137 | 7/2007 |
| WO | 2007/093643 | 8/2007 |
| WO | 2008/091670 | 7/2008 |

OTHER PUBLICATIONS

Baier et al., "Intermolecular energy transfer after vibrational excitation of a perylene dye in solution, in polymer binder, and in a side-chain copolymer," *J. Chem. Phys.*, 114: 6739-6743 (2001).

Buncel et al., "Synthesis and characterization of [3,3]- and [3,4]-perinophane," *Tetrahedron Letters*, 42:3559-3562 (2001).

Chen et al., "Oligothiophene-Functionalized Perylene Bisimide System: Synthesis, Characterization, and Electrochemical Polymerization Properties," *Chem. Mater.*, 17:2208-2215 (2005).

Facchetti et al., "Building Blocks for n-Type Organic Electronics. Regiochemically Modulated Inversion of Majority Carrier Sign in Perfluoroarene-Modified Polythiophene Conductors," *Angew. Chem. Int. Ed.*, 2003:42, 3900-3903.

Facchetti et al., "n-Type Building Blocks for Organic Electronics: a Homologous Family of Fluorocarbon-substituted Thiophene Oligomers with High Carrier Mobility," *Adv. Mater.*, 2003: 15, 33-38.

Facchetti et al., "Tuning the Semiconducting Properties of Sexithiophene by a,w-Substitution—$\alpha$,w-Diperfluorohexylsexithiophene: the First n-Type Sexithiophene for Thin-film Transistors," *Angew. Chem. Int. Ed*, 2000: 39, 4547-4551.

Giaimo et al., "Excited-State Symmetry Breaking in Cofacial and Linear Dimers of a Green Perylenediimide Chlorophyll Analogue Leading to Ultrafast Charge Separation," *J. Am. Chem. Soc.*, 124: 8530-8531 (2002).

Holman et al., "Studying and Switching Electron Transfer: From the Ensemble to the Single Molecule," *J. Am. Chem. Soc.*, 126: 16126-16133 (2004).

Huttner et al., "N-type organic field effect transistors from perylene bisimide block copolymers and homopolymers," *Appl. Phys. Lett.*, 92: 093302 (2008).

Jones et al., "Cyanonaphthalene Diimide Semiconductors for Air-Stable, Flexible, and Optically Transparent n-Channel Field-Effect Transistors," *Chem. Mater.*, 19(11):2703-2705 (2007).

Jones et al., "High-Mobility Air-Stable n-Type Dicyanoperylene-3,4:9,10-bis(dicarboximides)," *Agnew., Chem. Int. Ed.*, 43:6363-6366 (2004).

Jones et al., "Tuning Orbital Energetics in Arylene Diimide Semiconductors. Materials Design for Ambient Stability of n-Type Charge Transport," *J. Am. Chem. Soc.*, 2007: 129, 15259-15278.

Kwan et al., "Electrochemistry of Langmuir-Blodgett and Self-Assembled Films Built from Oligoimides," *Langmuir*, 8:3003-3007 (1992).

Langhals et al., "Tangentially Coupled $\pi$ Systems and their Through-Space Interaction—Trichromophoric Perylene Dyes," *J. Prakt. Chem.*, 338: 654-659 (1996).

Langhals et al., "Chiral Bifluorophoric Perylene Dyes with Unusually High CD Effects—A Simple Model for the Photosynthesis Reaction Center," *Leibigs Ann./Recueil.*, 1151-1153 (1997).

Lindner et al., "Nanostructures of N-type organic semiconductor in a p-type matrix via self-assembly of block copolymers," *Macromolecules*, 37:8832-8835 (2004).

Lindner et al., "Charge Separation at Self-Assembled Nanostructured Bulk Interface in Block Copolymers," *Angew. Chem. Int. Ed.*, 45:3364-3368 (2006).

Lukas et al., "Femtosecond Optical Switching of Electron Transport Direction in Branched Donor-Acceptor Arrays," *J. Phys. Chem. B*, 104: 931-940 (2000).

Lukas et al., "Biomimetic Electron Transfer Using Low Energy Excited States: A Green Perylene-Based Analogue of Chloroophyll a," *J. Phys. Chem. B*, 106: 1299-1306 (2002).

Martyushina et al., "Searches for Nondepolarizing Short-Action Myorelaxants," *Pharm. Chem.*, 1982: 16 (7), 801-806 (English translation).

Morris et al., "Synthesis of Extended Linear Aromatics Using Tandem Diels-Alder Aromatization Reactions," *J. Org. Chem.*, 59:6484-6486 (1994).

Müller et al., "Facile synthetic approach to novel core-extended perylene carboximide dyes," *Chem. Commun.*, (2005) 4045-4046.

Petit et al., "Synthesis of macromolecular substances comprising dye derivatives as monomeric units. III. Synthesis and study of monomeric dihydroxy dyes," *Bulletin de la Societe Chimique de France*, 7-8:1591-1596 (1974).

Rodriguez-Llorente et al., "Infrared and Raman spectra of thin solid films of 1,2-bis(propylimido perylene) ethane," *Spectrochimica Acta. Part A*, 55: 969-978 (1999).

Rodriguez-Llorente et al., "Vibrational spectra and thin solid films of a bi(propylperylenediimide)," *J. Mater. Chem.*, 8(10): 2175-2179 (1998).

Rodriguez-Llorente et al., "Spectroscopic characterization of thin solid films of a bis(chlorobenzylimidoperyleneimido)octane derivative," *J. Mater. Chem.*, 8(3): 629-632 (1998).

Rohr et al., "Liquid crystalline coronene derivatives," *J. Mater. Chem.*, 11:1789-1799 (2001).

Shimizu et al., "Convergent Functional Groups. 15. Synthetic and Structural Studies of Large and Rigid Molecular Clefts," *J. Am. Chem. Soc.*, 116:5145-5149 (1994).

Singh et al., "Soluble derivatives of perylene and naphthalene diimide for n-channel organic field-effect transistors," *Organic Electronics*, 7:480-489 (2006).

Tauber et al., "Electron Hopping in π-Stacked Covalent and Self-Assembled Perylene Diimides Observed by ENDOR Spectroscopy," *JACS Comm.*, 128: 1782-1783.

Thalacker et al., "Hydrogen bond directed self-assembly of core-substituted naphthalene bisimides with melamines in solution and at the graphite interface," *Org. Biomol. Chem.*, 3:414-422 (2005).

Tsoi et al., "Distributed Bilayer Photovoltaics Based on Nematic Liquid Crystal Polymer Networks," *Chem. Mater.*, 19:5475-5484 (2007).

Database Caplus [Online] Chemical Abstracts Service, Columbus, Ohio, US; May 12, 1984, XP002493285 retrieved from STN Database accession No. 1984:34294 abstract.

Database WPI Thomson Scientific, London, GB; AN 1983-750663 XP002493286 and JP 58 124790 A (Matsushita Electric Ind. Co. Ltd.) Jul. 25, 1983 abstract.

\* cited by examiner

METHODS FOR PREPARING ARENE-BIS (DICARBOXIMIDE)-BASED SEMICONDUCTING MATERIALS AND RELATED INTERMEDIATES FOR PREPARING SAME

CROSS REFERENCE TO RELATED APPLICATION

This application claims priority to and the benefit of U.S. Provisional Patent Application Ser. No. 60/879,145, filed on Jan. 8, 2007, the disclosure of which is incorporated by reference in its entirety.

INTRODUCTION

Organic molecules based on arene-bis(dicarboximide)s (QDIs) can be key elements in advanced optical and electronic materials. Examples of QDIs include perylene-bis(dicarboximide)s (PDIs), coronene-bis(dicarboximide)s (CDIs), naphthalene-bis(dicarboximide)s (NDIs), and anthracene-bis(dicarboximide)s (ADIs), structures of which are illustrated in FIG. 1. See e.g., Law, *Chem. Rev.*, 93: 449 (1993); Langhals et al., *Angew. Chem., Int. Ed.*, 44: 2427 (2005); Malenfant et al., *Appl. Phys. Lett.*, 80: 2517 (2002); Herrmann et al., *Chem. Lett.*, 35: 978 (2006); Ilhan et al., *Chem. Mater.*, 16: 2978 (2004); Bhattacharyya et al., *Synlett*, 1361 (2003); Langhals et al., *Chemistry*, 12: 2815 (2006); Kelley et al. *J. Am. Chem. Soc.*, 128: 4779 (2006); Adachi et al., *Appl. Phys. Lett.*, 56: 799 (1990); and Katz et al. *J. Am. Chem. Soc.*, 122: 7787 (2000). The properties of these QDIs can be modulated by molecular functionalization, for example, at the nitrogen atoms of the imide groups and/or on the arene core.

Applications of functionalized QDIs have been found in light-harvesting arrays, photovoltaic cells, organic field-effect transistors, and organic light-emitting diodes. These molecules also have been reported to be building blocks for constructing supramolecular or giant-molecular systems. Among core-substituted QDIs, cyanated PDIs, NDIs, and ADIs have been demonstrated to be important materials for the fabrication of a number of organic semiconductor-based devices, including field-effect transistors, complementary circuits, ring oscillators, and D-flipflops, as well as solar cells. See e.g., Jung et al., *Appl. Phys. Lett.*, 88: 183102/1 (2006); and Yoo et al., *Appl. Phys. Lett.*, 88: 082104 (2006).

In general, the preparation of N,N'-disubstituted core-substituted arene-bis(dicarboximide)s follows the synthetic route shown in FIG. 2. The first step is usually the functionalization at the imide nitrogen atoms. For example, an appropriate dianhydride (QDA) can be reacted with a primary amine ($R^1$—$NH_2$) to provide the corresponding dicarboximide (QDIR$^1$). See e.g., Osswald et al., *Angew. Chem., Int. Ed.*, 44: 250 (2005); Segura et al., *Org. Lett.*, 7: 2345 (2005); Rohr et al., *Angew. Chem., Int. Ed.*, 37: 1434 (1998); Qu et al., *Angew. Chem., Int. Ed.*, 43: 1528 (2004); Müller et al., *Chem. Commun.*, 4045 (2005); Rybtchinski et al., *J. Phys. Chem.*, 108: 7497 (2004); and Vysotsky et al., *Org. Lett.*, 4: 2901 (2002). An alternative method is to convert the dianhydride to an unsubstituted dicarboximide (QDIH) with ammonia ($NH_3$), followed by functionalization of the imide nitrogen with $R^1$-LG. See e.g., Pasaogullari et al., *Dyes and Pigments*, 69: 118 (2006); Patrick et al., *Dyes and Pigments*, 55: 123 (2002); Chernick et al., *J. Org. Chem.*, 70: 1486 (2005); Fan et al., *Synth. Met.*, 145: 203 (2004).

The second step is the functionalization of the core positions (QDI-$R^a_n$) via uncatalyzed or metal-catalyzed substitution of the corresponding halogenated QDI precursors (QDI-$X_n$). For instance, the halo groups in a QDI-$X_n$ precursor can be displaced with aryl, cyano, phenoxy, and/or amino groups to provide the corresponding QDI-$R^a_n$. See e.g., Würthner et al., *J. Org. Chem.*, 69: 7933 (2004); and German Patent Application Nos. DE 3434059 and DE 19547209.

As shown in FIG. 2, both of the syntheses require the functionalization of the imide nitrogen atoms before any of the core positions. To allow efficient screening of N,N'-disubstituted QDI-$R^a_n$ derivatives with identical functionalized core but different imide nitrogen substitutions, a more effective synthetic method is desired. An example of such method can include functionalization on the core positions of a dianhydride starting material followed by conversion of the dianhydride to a disubstituted diimide. In practice, very few core-substituted dianhydrides (QDA-$R^a_n$) or core-substituted diimides (QDIH-$R^a_n$) are known and no examples of QDA-$R^a_n$ and QDIH-$R^a_n$ where $R^a$ is an electron-withdrawing group (EWG) have been reported. Furthermore, most QDAs and QDIHs, when substituted in the core with electron-withdrawing groups, are likely to be unstable upon reaction with strong nucleophiles such as primary amines under standard reaction conditions.

SUMMARY

In light of the foregoing, the present teachings provide new synthetic routes for preparing core-functionalized QDIs and the corresponding N,N'-disubstituted derivatives, which can address various deficiencies and shortcomings of the prior art, including those outlined above.

More specifically, the present teachings provide QDAs and QDIHs having various electron-withdrawing substituents in the core and methods of converting such core-substituted QDAs and QDIHs to N,N'-disubstituted QDIs.

In one aspect, the present teachings provide compounds of formulae I or II:

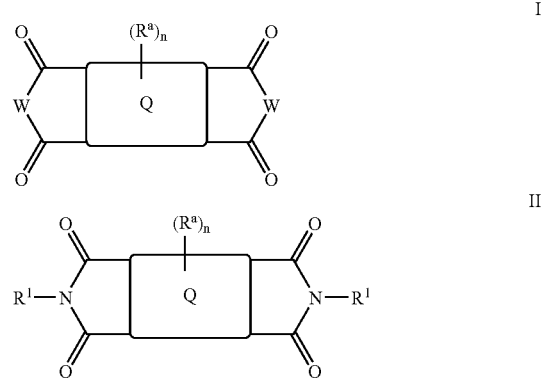

where Q, $R^a$, $R^1$, W, and n are as defined herein.

In another aspect, the present teachings provide methods of preparing compounds of formulae I and II, including methods of preparing compounds of formula II from compounds of formula I.

The foregoing as well as other features and advantages of the present teachings will be more fully understood from the following figures, description, and claims.

BRIEF DESCRIPTION OF THE DRAWINGS

A skilled artisan will understand that the drawings described below are for illustration purposes only. The drawings are not intended to limit the scope of the present teachings in any way.

DETAILED DESCRIPTION

Figure 1:
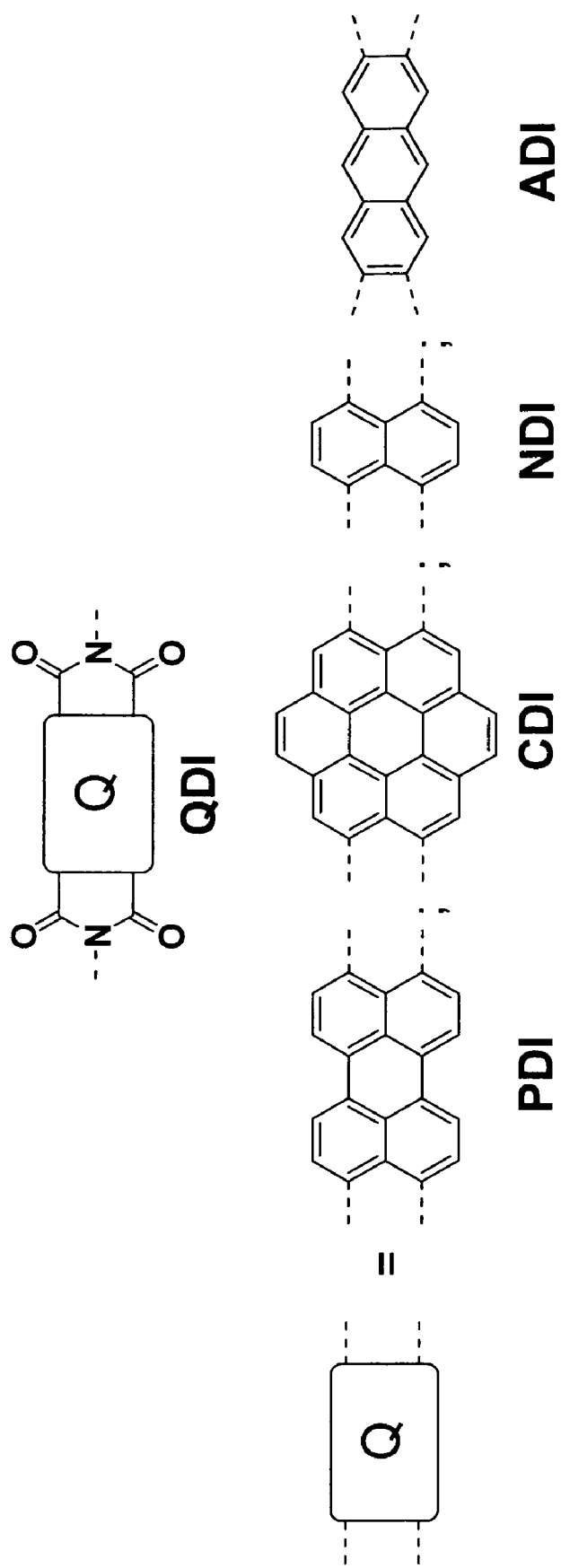
FIG. 1 shows the chemical structures of various examples of QDIs.
Figure 2:
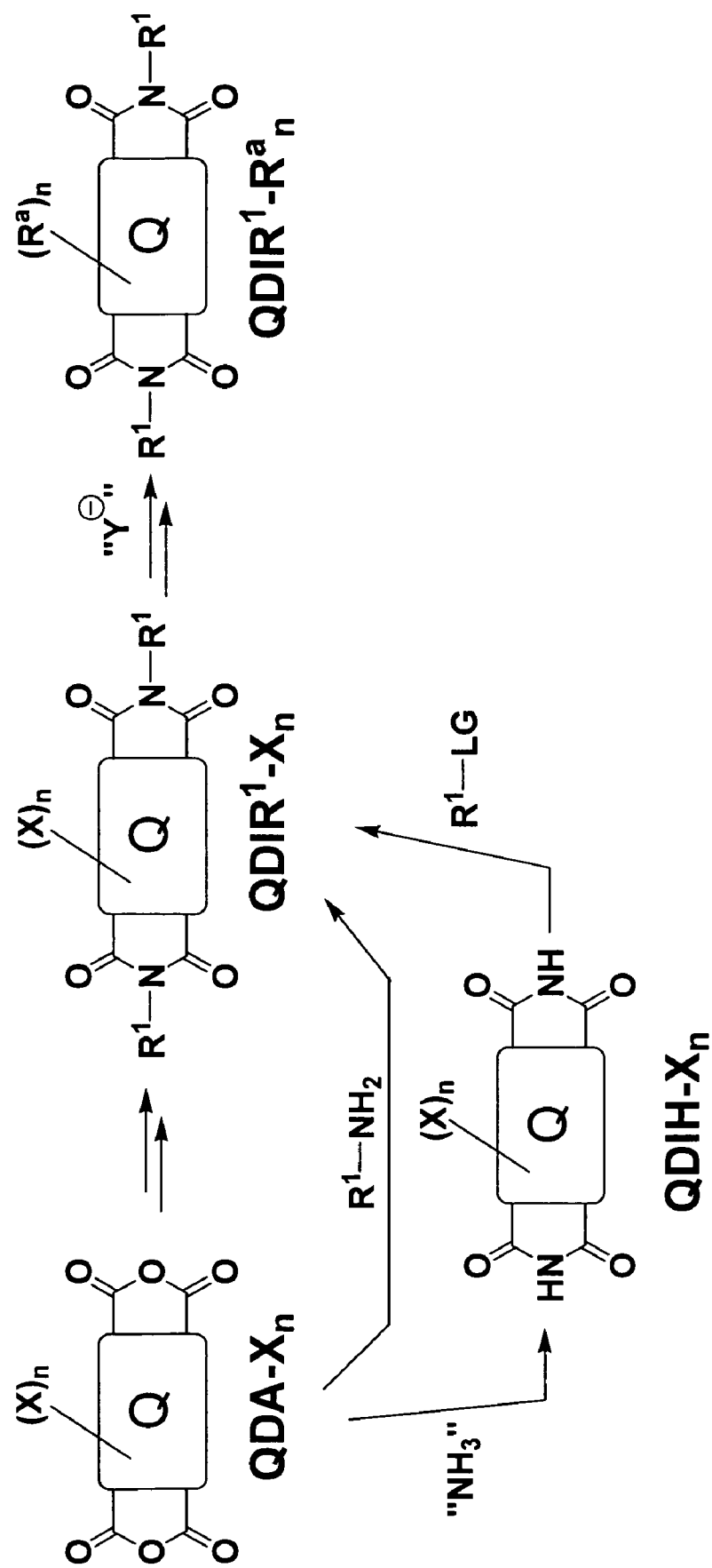
FIG. 2 illustrates known synthetic routes to core-substituted N,N'-disubstituted QDIs (QDIR$^1$-R$^a_n$).

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

The use of the terms "include," "includes," "including," "have," "has," or "having" should be generally understood as open-ended and non-limiting unless specifically stated otherwise.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

As used herein, "arene" or "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can include, without limitation, rylenes having the formula:

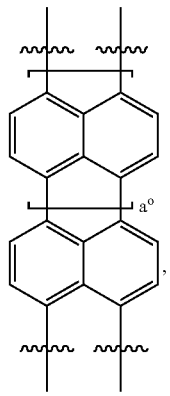

where a$^0$ can be an integer in the range of 0-3; coronenes having the formula:

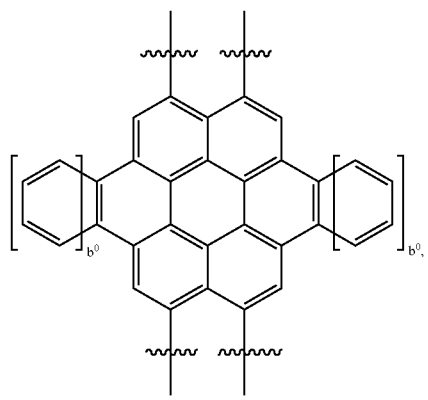

where b$^0$ can be an integer in the range of 0-3; and linear acenes having the formula:

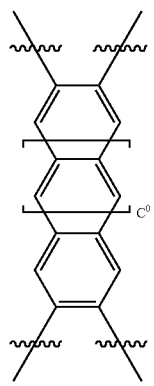

where c$^0$ can be an integer in the range of 0-4. The compounds disclosed herein typically have an arene or fused ring moiety core, which is tetravalent and can form covalent bonds with two moieties selected from —C(O)—O—C(O)—, —C(O)—NH—C(O)—, and —C(O)—NR$^1$—C(O)—, wherein R$^1$ is as defined herein. Such arene or fused ring moiety cores can be substituted with 1-8 R$^a$ groups, where R$^a$ is as defined herein.

As used herein, "dicarboximide" refers to a —C(O)—NH—C(O)— group, where the nitrogen atom can be substituted with an $R^1$ group as defined herein.

As used herein, "halo" or "halogen" refers to fluoro, chloro, bromo, and iodo.

As used herein, "amino" or "amine" refers to —NRR', where R and R' independently can be selected from H, an alkyl group, an arylalkyl group, an aryl group, a cycloalkyl group, a heteroaryl group, and a cycloheteroalkyl group, each of the alkyl group, the arylalkyl group, the aryl group, the cycloalkyl group, the heteroaryl group, and the cycloheteroalkyl group can be optionally substituted as described herein.

As used herein, "alkoxy" refers to an —O-alkyl group. Examples of alkoxy groups include, but are not limited to, methoxy, ethoxy, propoxy (e.g., n-propoxy and isopropoxy), t-butoxy groups, and the like.

As used herein, "alkylthio" refers to an —S-alkyl group. Examples of alkylthio groups include, but are not limited to, methylthio, ethylthio, propylthio (e.g., n-propylthio and isopropylthio), t-butylthio groups, and the like.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, isobutyl, sec-butyl, tert-butyl), pentyl groups (e.g., n-pentyl, isopentyl, neopentyl), and the like. In various embodiments, an alkyl group can have 1 to 20 carbon atoms, i.e., a $C_{1-20}$ alkyl group. In some embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In some embodiments, alkyl groups can be substituted as disclosed herein. An alkyl group is generally not substituted with another alkyl group or an alkenyl or alkynyl group.

As used herein, "haloalkyl" refers to an alkyl group having one or more halogen substituents. Examples of haloalkyl groups include, but are not limited to, $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-20}$ haloalkyl group can have the formula —$C_iX_{2i+1}$ or —$C_iH_{2i+1-j}X_j$, wherein X is F, Cl, Br, or I, i is an integer in the range of 1 to 20, and j is an integer in the range of 0 to 41, provided that j is less than or equal to 2i+1.

As used herein, "arylalkyl" refers to an -alkyl-aryl group, wherein the arylalkyl group is covalently linked to the defined chemical structure via the alkyl group. An arylalkyl group is within the definition of an -L-$C_{6-14}$ aryl group or a —Y—$C_{6-14}$ aryl group, where L and Y are independently divalent $C_{1-20}$ alkyl groups. An example of an arylalkyl group is a benzyl group (—$CH_2$—$C_6H_5$). An arylalkyl group can be optionally substituted, i.e., the aryl group and/or the alkyl group can be substituted, as disclosed herein.

As used herein, "alkenyl" refers to a straight-chain or branched alkyl group having one or more carbon-carbon double bonds. Examples of alkenyl groups include, but are not limited to, ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 20 carbon atoms, i.e., a $C_{2-20}$ alkenyl group. In some embodiments, alkenyl groups can be substituted as disclosed herein. An alkenyl group is generally not substituted with another alkenyl group or an alkyl or alkynyl group.

As used herein, "alkynyl" refers to a straight-chain or branched alkyl group having one or more triple carbon-carbon bonds. Examples of alkynyl groups include, but are not limited to, ethynyl, propynyl, butynyl, pentynyl, and the like. The one or more triple carbon-carbon bonds can be internal (such as in 2-butyne) or terminal (such as in 1-butyne). In various embodiments, an alkynyl group can have 2 to 20 carbon atoms, i.e., a $C_{2-20}$ alkynyl group. In some embodiments, alkynyl groups can be substituted as disclosed herein. An alkynyl group is generally not substituted with another alkynyl group or an alkyl group or an alkenyl group.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Examples of cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In various embodiments, a cycloalkyl group can have 3 to 14 carbon atoms, including 3 to 10 carbon atoms (i.e., a $C_{3-10}$ cycloalkyl group). In some embodiments, cycloalkyl groups can be substituted as disclosed herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, N, and S, and optionally contains one or more double or triple bonds. In various embodiments, a cycloheteroalkyl group can have 3 to 20 ring atoms, including 3 to 14 ring atoms (i.e., a 3-14 membered cycloheteroalkyl group). One or more N or S atoms in a cycloheteroalkyl ring can be oxidized (e.g., morpholine N-oxide, thiomorpholine S-oxide, thiomorpholine S,S-dioxide). In some embodiments, nitrogen atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as disclosed herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 16 carbon atoms in its ring system, which can include multiple fused rings. In some embodiments, a polycyclic aryl group can have from 7 to 16 carbon atoms. The aryl group can be covalently linked to the defined chemical structure at any suitable ring position that results in a stable structure. Examples of aryl groups having only aromatic carbocyclic ring(s) include, but are not limited to, phenyl, 1-naphthyl (bicyclic), 2-naphthyl (bicyclic), anthracenyl (tricyclic), phenanthrenyl (tricyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include, but are not limited to, benzodioxanyl, benzodioxolyl, chromanyl, indolinyl groups, and the like. In some embodiments, aryl groups can be substituted as disclosed herein. In some embodiments, an aryl group can have one or more halogen substituents, and can be referred to as a "haloaryl" group. Perhaloaryl groups, i.e., aryl groups wherein all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least 1 ring heteroatom selected from O, N, and S or a polycyclic ring system where at least one of the rings present in the ring system is aromatic and contains at least 1 ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, from 5 to 16 ring atoms and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5-membered monocyclic and 5-6 bicyclic ring systems shown below:

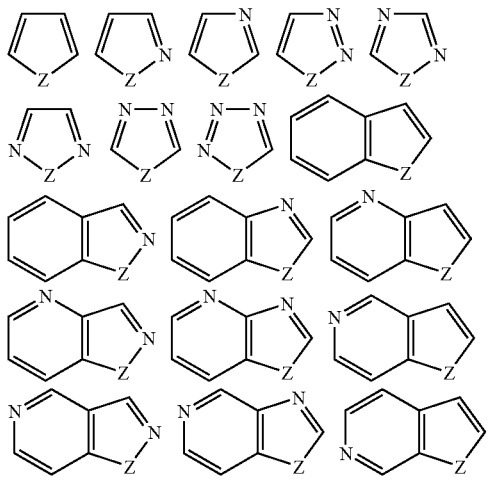

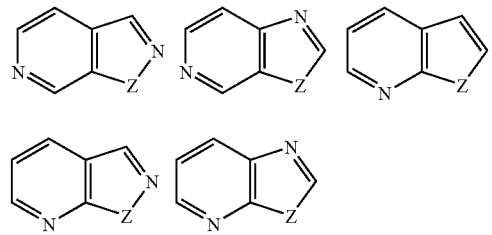

where Z is O, S, NH, N-alkyl, N-aryl, or N-(arylalkyl) (e.g., N-benzyl). Examples of heteroaryl groups include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxaloyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuryl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyrdazinyl, thienothiazolyl, thienooxazolyl, thienoimidazolyl, and the like. Further examples of heteroaryl groups include, but are not limited to, 4,5,6,7-tetrahydroindolyl, tetrahydroquinolyl, benzothienopyridyl, benzofuropyridyl, and the like. In some embodiments, heteroaryl groups can be substituted as disclosed herein.

As used herein, a "divalent group" refers to a linking group capable of forming covalent bonds with two other moieties. For example, compounds of the present teachings can include a divalent $C_{1-20}$ alkyl group, such as, for example, a methylene group.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halide (e.g., Cl, Br, I), azide ($N_3$), thiocyanate (SCN), nitro ($NO_2$), cyanate (CN), tosylate (toluenesulfonate, OTs), mesylate (methanesulfonate, OMs), brosylate (p-bromobenzenesulfonate, OBs), nosylate (4-nitrobenzenesulfonate, ONs), water ($H_2O$), ammonia ($NH_3$), and triflate (trifluoromethanesulfonate, OTf).

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein. It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halide (e.g., F, Cl, Br, I), —NO$_2$, —CN, —OH, —OR$^o$, —SH, —SR$^o$, —S(R$^o$)$_2^+$, —NH$_2$, —NHR$^o$, —NR$^o_2$, —N(R$^o$)$_3^+$, —SO$_3$H, —SO$_2$R$^o$, —SO$_3$R$^o$, —SO$_2$NHR$^o$, —SO$_2$N(R$^o$)$_2$, —COOH, —COR$^o$, —COOR$^o$, —CONHR$^o$, —CON(R$^o$)$_2$, $C_{1-10}$ haloalkyl groups, $C_{6-14}$ aryl groups, and 5-14 membered heteroaryl groups, where R$^o$ is a $C_{1-10}$ alkyl group, a $C_{2-10}$ alkenyl group, a $C_{2-10}$ alkynyl group, a $C_{1-10}$ haloalkyl group, a $C_{1-10}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

Compounds described herein can contain an asymmetric atom (also referred as a chiral center) and some of the compounds can contain one or more asymmetric atoms or centers, which can thus give rise to optical isomers (enantiomers) and diastereomers. The present teachings include such optical isomers (enantiomers) and diastereomers (geometric isomers), as well as the racemic and resolved, enantiomerically pure (+) and (−) stereoisomers, as well as other mixtures of the (+) and (−) stereoisomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes and imines). It is also understood that the present teachings encompass all possible regioisomers in pure form and mixtures thereof, which can be obtained by using standard separation procedures known to those skilled in the art, including, for examples, column chromatography, thin-layer chromatography, simulated moving-bed chromatography, and high-performance liquid chromatography. For example, perylene compounds of the present teachings can include any perylene derivatives in their respective pure forms or mixtures thereof, where the perylene derivatives can be substituted with 1, 2, 3, 4, 5, 6, 7, or 8 R$^a$ groups, and R$^a$ is as defined herein. Specifically, the perylene derivatives can include compounds having the moiety:

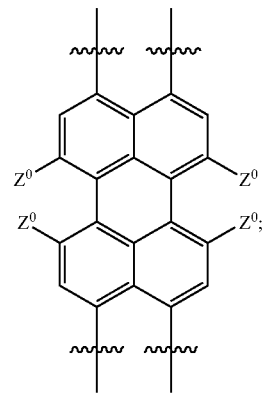

where Z$^o$, at each occurrence, can be H, an electron-withdrawing group, or a leaving group, where the electron-withdrawing group and the leaving group are as defined herein. In various embodiments, two of the Z$^o$ groups can be H and the other two Z$^o$ groups independently can be an electron-withdrawing group or a leaving group. Accordingly, in the embodiments where two of the Z$^o$ groups are H and the other two independently are an electron-withdrawing group or a leaving group, compounds of the present teachings can have regioisomers having the moieties:

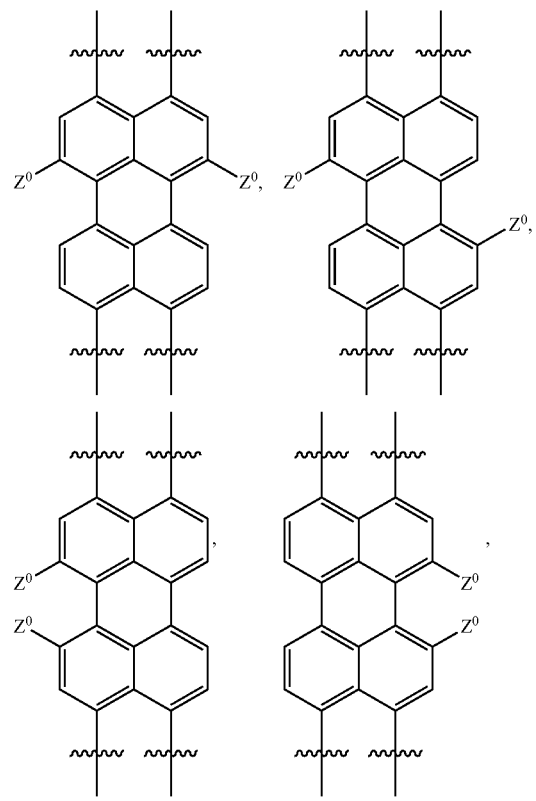

-continued

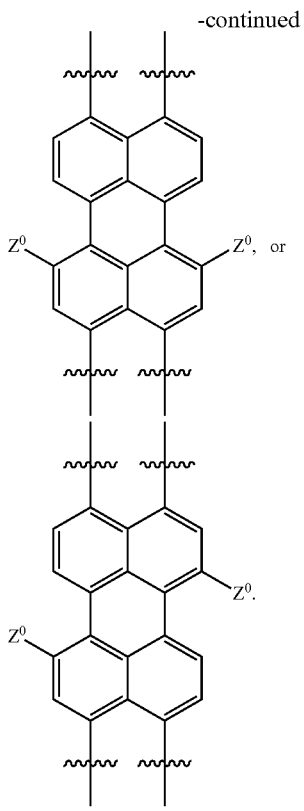

In certain embodiments, compounds of the present teachings can include regioisomers having the moieties:

i

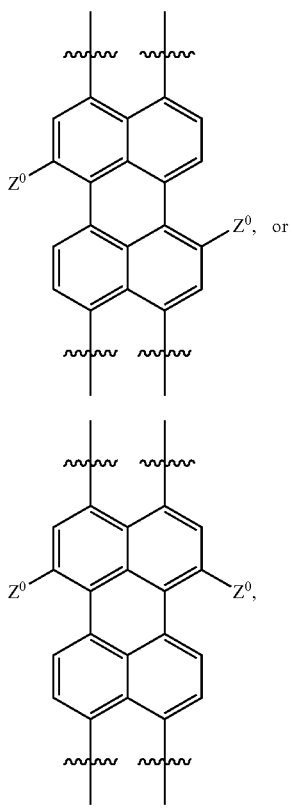

ii and mixtures thereof, where $Z^o$ independently can be an electron-withdrawing group or a leaving group, for example, a halogen such as Br or a CN group. In particular embodiments, $Z^o$ can be $R^a$ where $R^a$ is as defined herein. Further, it is specifically contemplated that the depiction of one regioisomer includes the other regioisomer and any regioisomeric mixtures unless specifically stated otherwise. Accordingly, the use of compounds of formula i include compounds of formula II (and vice versa) and mixtures of compounds of formulae i and ii.

As used herein, a "p-type semiconducting material" or a "p-type semiconductor" refers to a semiconducting material having holes as the majority current carriers. In some embodiments, when a p-type semiconducting material is deposited on a substrate, it can provide a hole mobility in excess of about $10^{-5}$ cm$^2$/Vs. In the case of field-effect devices, a p-type semiconductor can also exhibit a current on/off ratio of greater than about 10.

As used herein, a "n-type semiconducting material" or a "n-type semiconductor" refers to a semiconducting material having electrons as the majority current carriers. In some embodiments, when a n-type semiconducting material is deposited on a substrate, it can provide an electron mobility in excess of about $10^{-5}$ cm$^2$ Vs. In the case of field-effect devices, an n-type semiconductor can also exhibit a current on/off ratio of greater than about 10.

As used herein, "field effect mobility" refers to a measure of the velocity with which charge carriers, for example, holes (or units of positive charge) in the case of a p-type semiconducting material and electrons in the case of an n-type semiconducting material, move through the material under the influence of an electric field.

At various places in the present application temperatures are disclosed in ranges. It is specifically intended that the description includes narrower ranges of temperatures within such ranges, as well as the maximum and minimum temperatures embracing such range of temperatures.

Throughout the specification, structures may or may not be presented with chemical names. Where any question arises as to nomenclature, the structure prevails.

In one respect, the present teachings provide various arene derivatives. In various embodiments, the present teachings provide compounds of formula I:

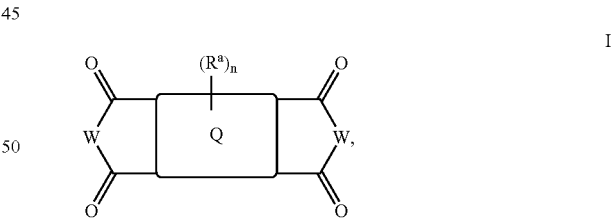

I wherein:
W, at each occurrence, is O or NH;
Q is a fused ring moiety;
$R^a$, at each occurrence, is selected from a) —CN, b) —NO$_2$, c) —C(O)R$^b$, d) —C(O)NHR$^b$, e) —C(O)OR$^b$, f) —S(O)R$^b$, g) —S(O)$_2$R$^b$, h) —S(O)$_2$OH, i) —(CF$_2$)$_r$R$^b$, j) —[C(CF$_3$)$_2$]$_r$R$^b$, k) oxo, and l) a 5-14 membered heteroaryl group substituted with 1-5 R$^c$ groups;
$R^b$, at each occurrence, is selected from a) H, b) a C$_{1-20}$ alkyl group, c) a C$_{3-10}$ cycloalkyl group, d) a C$_{6-14}$ aryl group, e) a C$_{7-20}$ arylalkyl group, f) a 3-12 membered cycloheteroalkyl group, and g) a 5-14 membered heteroaryl group, wherein each of the C$_{1-20}$ alkyl group, the C$_{3-10}$ cycloalkyl group, the $C_{6-14}$ aryl group, the $C_{7-20}$ arylalkyl group, the 3-12 membered cycloheteroalkyl group, and the 5-14 membered heteroaryl group optionally is substituted with 1-5 $R^c$ groups;

$R^c$, at each occurrence, is selected from a) a halogen, b) —CN, c) —NO$_2$, d) —C(O)H, e) —C(O)—C$_{1-20}$ alkyl, f) —C(O)NH$_2$, g) —C(O)NH—C$_{1-20}$ alkyl, h) —C(O)N(C$_{1-20}$ alkyl)$_2$, i) —C(O)OH, j) —C(O)—OC$_{1-20}$ alkyl, k) —S(O)H, l) —S(O)C$_{1-20}$ alkyl, m) —S(O)$_2$H, n) —S(O)$_2$—C$_{1-20}$ alkyl, and o) —S(O)$_2$OH;

n is 1, 2, 3, 4, 5, 6, 7, or 8; and t, at each occurrence, is 1, 2, 3, 4, 5, 6, 7, 8, 9, or 10.

In some embodiments, Q-$(R^a)_n$ can be:

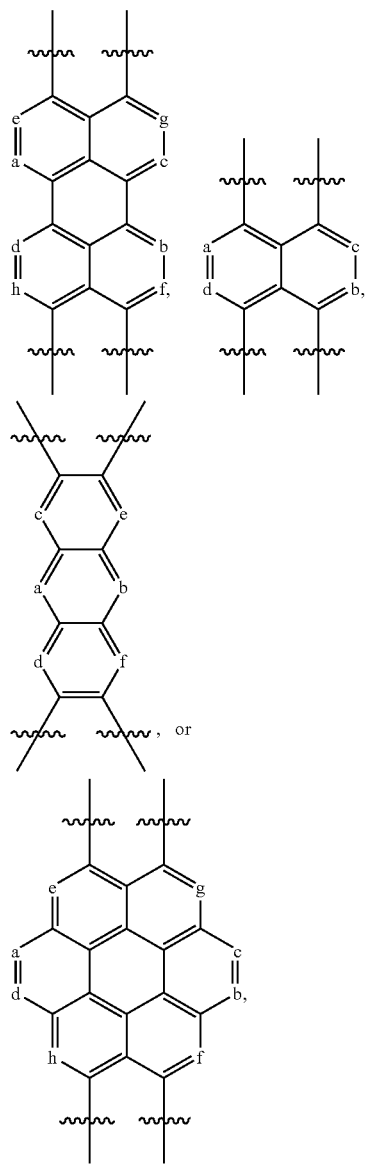

where a, b, c, d, e, f, g, and h, at each occurrence, independently are CH, CR$^a$, SiH, SiR$^a$, N, or P, and R$^a$ is as defined herein. For example, R$^a$ can be —CN, —NO$_2$, or —C(O)CH$_3$, and a, b, c, d, e, f, g, and h, at each occurrence, can independently be CH, C(CN), or C[C(O)CH$_3$]. In some embodiments, Q can be substituted with 2-4 R$^a$ groups. In particular embodiments, Q can be substituted at the central "bay" positions, i.e., Q-$(R^a)_n$ can be:

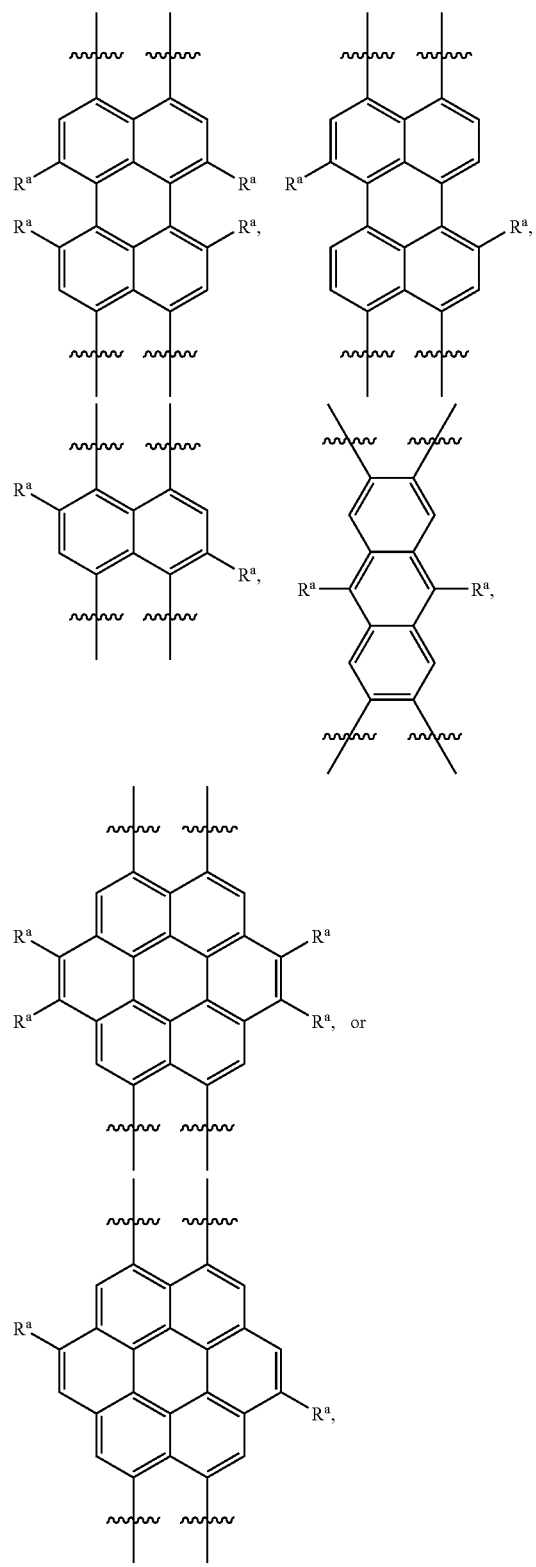

wherein R$^a$ is as defined herein. For example, R$^a$ can be —CN.

In particular embodiments, the compounds of the present teachings can have the formula:

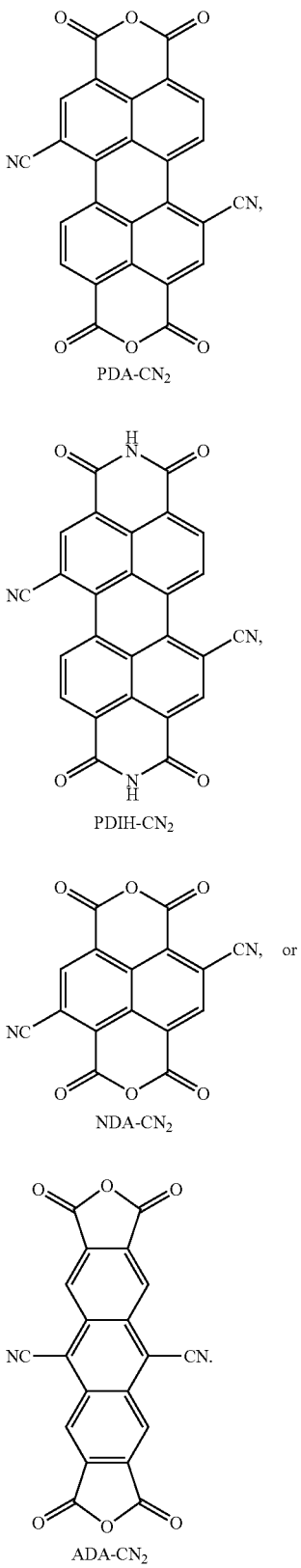

PDA-CN₂

PDIH-CN₂

NDA-CN₂

ADA-CN₂

In various embodiments, the present teachings provide compounds of formula II:

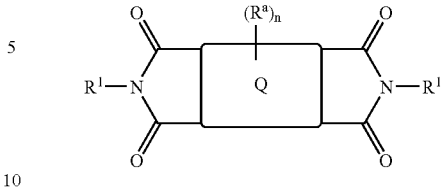

II wherein:

Q is a fused ring moiety;

$R^a$, at each occurrence, is selected from a) —CN, b) —NO₂, c) —C(O)$R^b$, d) —C(O)NH$R^b$, e) —C(O)O$R^b$, f) —S(O)$R^b$, g) —S(O)₂$R^b$, h) —S(O)₂OH, i) —(CF₂)$_t R^b$, j) —[C(CF₃)₂]$_t R^b$, k) oxo, and l) a 5-14 membered heteroaryl group substituted with 1-5 $R^c$ groups;

$R^b$, at each occurrence, is selected from a) H, b) a $C_{1-20}$ alkyl group, c) a $C_{3-10}$ cycloalkyl group, d) a $C_{6-14}$ aryl group, e) a $C_{7-20}$ arylalkyl group, f) a 3-12 membered cycloheteroalkyl group, and g) a 5-14 membered heteroaryl group, wherein each of the $C_{1-20}$ alkyl group, the $C_{3-10}$ cycloalkyl group, the $C_{6-14}$ aryl group, the $C_{7-20}$ arylalkyl group, the 3-12 membered cycloheteroalkyl group, and the 5-14 membered heteroaryl optionally is substituted with 1-5 $R^c$ groups;

$R^c$, at each occurrence, is selected from a) a halogen, b) —CN, c) —NO₂, d) —C(O)H, e) —C(O)—$C_{1-20}$ alkyl, f) —C(O)NH₂, g) —C(O)NH—$C_{1-20}$ alkyl, h) —C(O)N($C_{1-20}$ alkyl)₂, i) —C(O)OH, j) —C(O)—O$C_{1-20}$ alkyl, k) —S(O)H, l) —S(O)—$C_{1-20}$ alkyl, m) —S(O)₂H, n) —S(O)₂—$C_{1-20}$ alkyl, and o) —S(O)₂OH;

n is 1, 2, 3, 4, 5, 6, 7, or 8;

t, at each occurrence, is 1, 2, 3, 4, 5, 6, 7, 8, 9, or 10;

$R^1$, at each occurrence, is -L-$R^2$ or -L-$Ar^1$—$R^2$;

L, at each occurrence, is Y or (CH₂CH₂O)$_p$;

Y, at each occurrence, is a divalent $C_{1-20}$ alkyl group, a divalent $C_{1-20}$ haloalkyl group, or a covalent bond;

$Ar^1$ is a $C_{6-14}$ aryl group or a 5-14 membered heteroaryl group, each optionally substituted with 1-5 substituents independently selected from a halogen, —CN, a $C_{1-20}$ alkyl group, a $C_{2-20}$ alkenyl group, a $C_{1-20}$ alkoxy group, and a $C_{1-20}$ haloalkyl group;

$R^2$, at each occurrence, is selected from a) —O$R^d$, b) —C(O)O$R^d$, c) —(O)$R^e$, d) —C(O)N$R^e R^f$, e) —C(S)O$R^d$, f) —C(S)$R^e$, g) —C(S)N$R^e R^f$, h) —S$R^d$, i) —S(O)₂O$R^d$, j) —S(O)₂$R^e$, k) —S(O)₂N$R^e R^f$, l) a $C_{1-20}$ alkyl group, m) a $C_{2-20}$ alkenyl group, n) a $C_{2-20}$ alkynyl group, o) a $C_{3-10}$ cycloalkyl group, p) a $C_{6-14}$ aryl group, q) a 3-12 membered cycloheteroalkyl group, and r) a 5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group optionally is substituted with 1-5-L-$R^3$ or -L-$Ar^2$—$R^3$ groups;

$R^d$, at each occurrence, is selected from a) H, b) —C(O)$R^e$, c) —C(O)N$R^e R^f$, d) —C(S)$R^e$, e) —C(S)N$R^e R^f$, f) a $C_{1-20}$ alkyl group, g) a $C_{2-20}$ alkenyl group, h) a $C_{2-20}$ alkynyl group, i) —Y—$C_{3-10}$ cycloalkyl group, j) —Y—$C_{6-14}$ aryl group, k) —Y-3-12 membered cycloheteroalkyl group, and l) —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group optionally is substituted with 1-5-L-$R^3$ groups;

$R^e$ and $R^f$, at each occurrence, independently are selected from a) H, b) —OH, c) —SH, d) —S(O)$_2$OH, e) —C(O)OH, f) —C(O)NH$_2$, g) —C(S)NH$_2$, h) —OC$_{1-20}$ alkyl, i) —O—Y—C$_{6-14}$ aryl, j) —C(O)—C$_{1-20}$ alkyl, k) —C(O)OC$_{1-20}$ alkyl, l) —C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl)-Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl)-Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, and ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-5-L-R$^3$ groups;

Ar$^2$, at each occurrence, is a C$_{6-14}$ aryl group or a 5-14 membered heteroaryl group, each optionally substituted with 1-5 substituents independently selected from a halogen, —CN, a C$_{1-20}$ alkyl group, a C$_{2-20}$ alkenyl group, a C$_{1-20}$ haloalkyl group, and a C$_{1-20}$ alkoxy group;

R$^3$, at each occurrence, is selected from a) halogen, b) —CN, c) —NO$_2$, d) oxo, e) —OR$^g$, f) —SR$^g$, g) —NR$^g$R$^h$, h) —N(O)R$^g$R$^h$, i) —S(O)$_m$R$^g$, j) —S(O)$_m$OR$^g$, k) —S(O)$_m$N-R$^g$R$^h$, l) —C(O)R$^g$, m) —C(O)OR$^g$, n) —C(O)NR$^g$R$^h$, o) —C(S)NR$^g$R$^h$, p) —SiH$_3$, q) —SiH(C$_{1-2}$ alkyl)$_2$, r) —SiH$_2$(C$_{1-20}$ alkyl), s) —Si(C$_{1-20}$ alkyl)$_3$, t) a C$_{1-20}$ alkyl group, u) a C$_{2-20}$ alkenyl group, v) a C$_{2-20}$ alkynyl group, w) a C$_{3-10}$ cycloalkyl group, x) a C$_{6-14}$ aryl group, y) a 3-12 membered cycloheteroalkyl group, or z) a 5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-5-L-R$^4$ groups;

R$^g$ and R$^h$, at each occurrence, independently are selected from a) H, b) —OH, c) —SH, d) —S(O)$_2$OH, e) —C(O)OH, f) —C(O)NH$_2$, g) —C(S)NH$_2$, h) —OC$_{1-20}$ alkyl, i) —O—Y—C$_{6-14}$ aryl, j) —C(O)—C$_{1-20}$ alkyl, k) —C(O)—OC$_{1-20}$ alkyl, l) —C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl)-Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl)-Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, and ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-5-L-R$^4$ groups;

R$^4$, at each occurrence, is selected from a) halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —N(C$_{1-20}$ alkyl)-Y—C$_{6-14}$ aryl, j) —N(—Y—C$_{6-14}$ aryl)$_2$, k) —S(O)$_m$H, l) —S(O)$_m$C$_{1-20}$ alkyl, m) —S(O)$_2$OH, n) —S(O)$_m$—OC$_{1-20}$ alkyl, o) —S(O)$_m$—O—Y—C$_{6-14}$ aryl, p) —CHO, q) —C(O)—C$_{1-20}$ alkyl, r) —C(O)—C$_{6-14}$ aryl, s) —C(O)OH, t) —C(O)—OC$_{1-20}$ alkyl, u) —C(O)—O—Y—C$_{6-14}$ aryl, v) —C(O)NH$_2$, w) —C(O)NH—C$_{1-12}$ alkyl, x) —C(O)N(C$_{1-20}$ alkyl)$_2$, y) —C(O)NH—Y—C$_{6-14}$ aryl, z) —C(O)N(C$_{1-20}$ alkyl)-Y—C$_{6-14}$ aryl, aa) —C(O)N(—Y—C$_{6-14}$ aryl)$_2$, ab) —C(S)NH$_2$, ac) —C(S)NH—C$_{1-20}$ alkyl, ad) —C(S)N(C$_{1-20}$ alkyl)$_2$, ae) —C(S)N(—Y—C$_{6-14}$ aryl)$_2$, af) —C(S)N(C$_{1-20}$ alkyl)-Y—C$_{6-14}$ aryl, ag) —C(S)NH—Y—C$_{6-14}$ aryl, ah) —S(O)$_m$NH$_2$, ai) —S(O)$_m$NH(C$_{1-20}$ alkyl), aj) —S(O)$_m$N(C$_{1-20}$ alkyl)$_2$, ak) —S(O)$_m$NH(—Y—C$_{6-14}$ aryl), al) —S(O)$_m$N(C$_{1-20}$ alkyl)-Y—C$_{6-14}$ aryl, am) —S(O)$_m$N(—Y—C$_{6-14}$ aryl)$_2$, an)—SiH$_3$, ao) —SiH(C$_{1-20}$ alkyl)$_2$, ap) —SiH$_2$(C$_{1-20}$ alkyl), ar) —Si(C$_{1-20}$ alkyl)$_3$, as) a C$_{1-20}$ alkyl group, at) a C$_{2-20}$ alkenyl group, au) a C$_{2-20}$ alkynyl group, av) a C$_{1-20}$ alkoxy group, aw) a C$_{1-20}$ haloalkyl group, ax) a C$_{3-10}$ cycloalkyl group, ay) a C$_{6-14}$ aryl group, az) a 3-12 membered cycloheteroalkyl group, and ba) a 5-14 membered heteroaryl group;

m, at each occurrence, is 0, 1, or 2; and p, at each occurrence, is 0, 1, 2, 3, 4, 5, 6, 7, 8, 9, 10, 11, 12, 13, 14, 15, 16, 17, 18, 19, or 20.

In some embodiments, Q-(R$^a$)$_n$ can be:

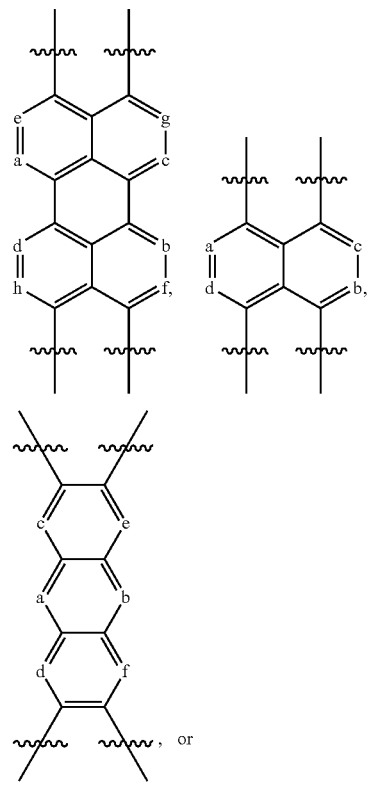

-continued

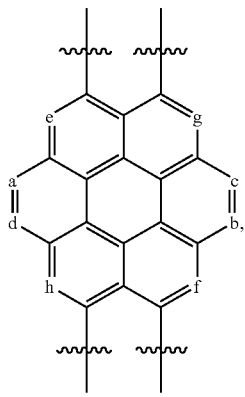

where a, b, c, d, e, f, g, and h, at each occurrence, independently are CH, CR$^a$, SiH, SiR$^a$, N, or P, and R$^a$ is as defined herein. For example, R$^a$ can be —CN, —NO$_2$, or —C(O)CH$_3$, and a, b, c, d, e, f, g, and h, at each occurrence, can independently be CH, C(CN), or C[C(O)CH$_3$]. In some embodiments, Q can be substituted with 2-4 R$^a$ groups. In particular embodiments, Q can be substituted at the "bay" positions, i.e., Q-(R$^a$)$_n$ can be:

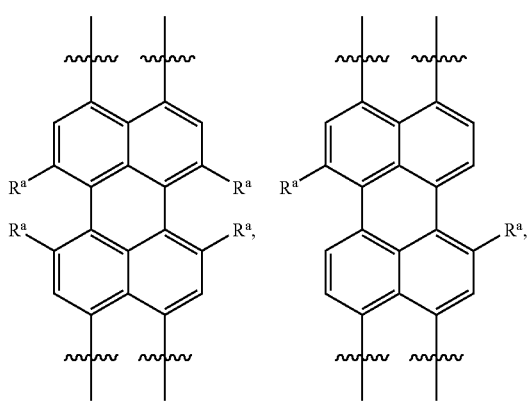

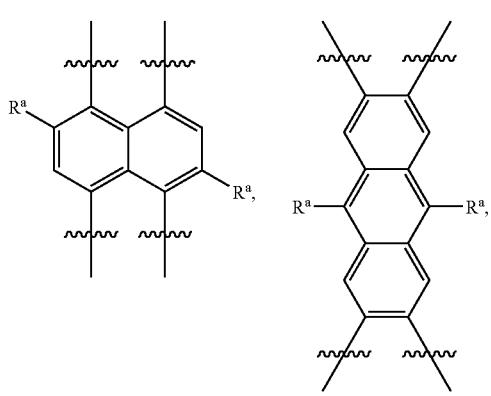

-continued

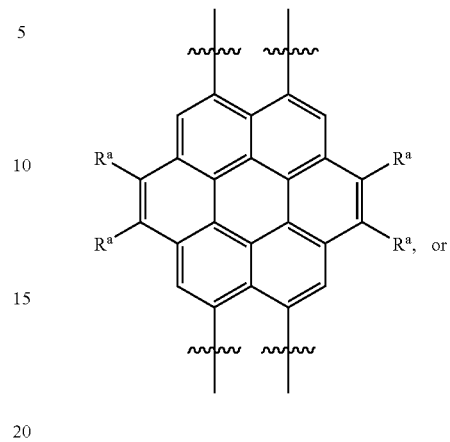

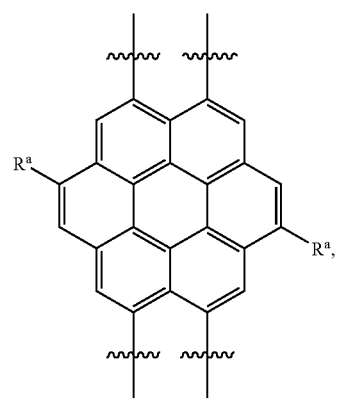

wherein R$^a$ is as defined herein. For example, R$^a$ can be —CN.

In particular embodiments, the compounds of the present teachings can have the formula:

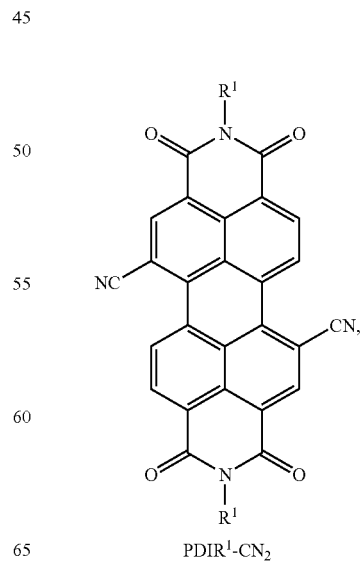

PDIR$^1$-CN$_2$

NDIR¹-CN₂

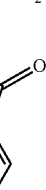

ADIR¹-CN₂

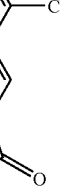

CDAR¹-CN₂ where R¹ is as defined herein.

In some embodiments, R¹ can be selected from a straight chain C₁₋₂₀ alkyl group, a branched C₁₋₂₀ alkyl group, a branched C₂₋₂₀ alkenyl group, a —Y—C₃₋₁₀ cycloalkyl group, a —Y—C₆₋₁₄ aryl group, a —Y-3-12 membered cycloheteroalkyl group, and a —Y-5-14 membered heteroaryl group, where each of the C₁₋₂₀ alkyl groups, the C₂₋₂₀ alkenyl group, the C₃₋₁₀ cycloalkyl group, the C₆₋₁₄ aryl group, the 3-12 membered cycloheteroalkyl group, and the 5-14 membered heteroaryl group can be optionally substituted with 1-5-L-R³ groups, and L and R³ are as defined herein.

In particular embodiments, R¹ can be selected from an n-octyl group, a (3S)-3,7-dimethyl-6-octenyl group, a (3S)-3,7-dimethyloctyl group, a 4-n-hexylphenyl group, a 4-picolyl group, a 6-tert-butyloxycarbonylaminohexyl group, a 9-anthracenyl group, an anthracene-9-ylmethyl group, and a 2-(anthracene-9-yl)-ethyl group.

In some embodiments, R¹ can be a branched C₁₋₂₀ alkyl group or a branched C₂₋₂₀ alkenyl group. In particular embodiments, R¹ can be

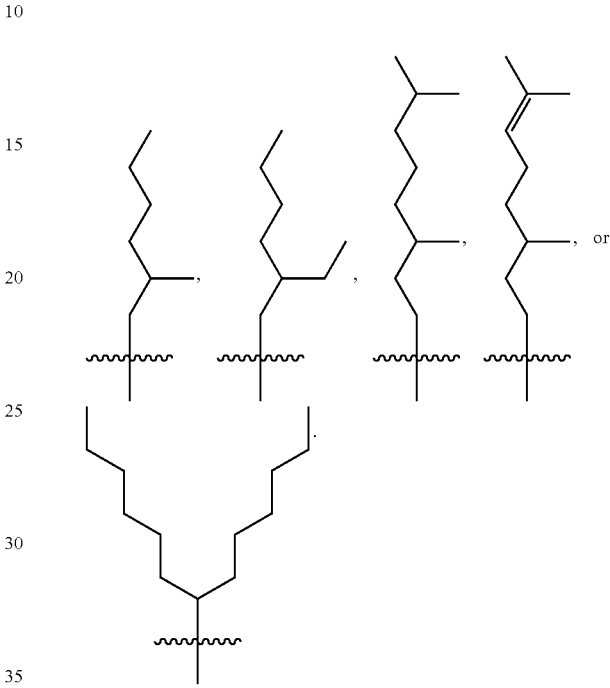

In various embodiments, R¹ can be -L-R² or -L-Ar¹—R², where R² can be a C₆₋₁₄ aryl group or a 5-14 membered heteroaryl group, each optionally substituted with 1-5-L-R³ or -L-Ar²—R³ groups; Ar¹ can be a C₆₋₁₄ aryl group or a 5-14 membered heteroaryl group, each optionally substituted with 1-5 substituents independently selected from halogen, —CN, a C₁₋₆ alkyl group, a C₁₋₆ alkoxy group, and a C₁₋₆ haloalkyl group; and L, Ar², and R³ are as defined herein. For example, R² and Ar¹ independently can be a C₆₋₁₄ aryl group optionally substituted as disclosed herein. In some embodiments, each of R² and A¹ can be a phenyl group (i.e., R² and Ar¹ together can form a biaryl group) optionally substituted with 1-5 substitution groups independently selected from a halogen, a C₁₋₂₀ alkyl group, a C₂₋₂₀ alkenyl group, a C₁₋₂₀ haloalkyl group, and a C₁₋₂₀ alkoxy group. In some embodiments, L can be a divalent C₁₋₁₀ alkyl group, a divalent C₁₋₁₀ haloalkyl group, or a covalent bond. In certain embodiments, R¹ can include at least one perhaloaryl group. For instance, R¹ can be a benzyl group, a biphenyl group, or a fluoro-substituted biphenyl group as shown below:

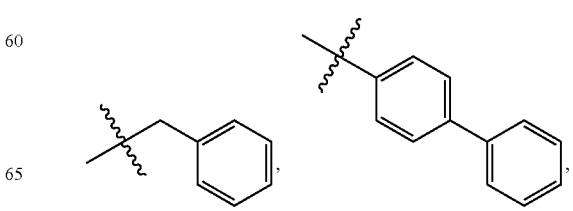

-continued

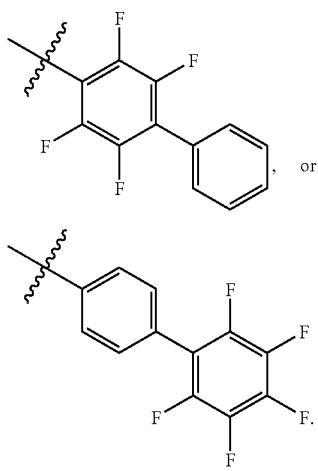

In certain embodiments, R¹ can be optionally substituted with an -L'-$C_{6-14}$ aryl group or an -L'-bi($C_{6-14}$ aryl) group, where L' can be a divalent $C_{1-10}$ alkyl group, —C(O)—, —O—, —S—, or —S(O)—, and each of the $C_{6-14}$ aryl groups can be optionally substituted with 1-5 groups independently selected from R³ and R⁴. In particular embodiments, R¹ can be:

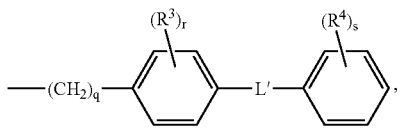

where q can be 0, 1, 2, 3, 4, 5, 6, 7, 8, 9, or 10, r can be 0, 1, 2, 3, or 4, s can be 0, 1, 2, 3, 4, or 5, and L', R³, and R⁴ are as defined herein. For example, q can be 0, 1, or 2, R³ can be a halogen (e.g., F), r can be 0, 1, 2, 3, or 4, s can be 0, 1, 2, 3, or 4, L' can be CH₂—, —CH₂CH₂—, —C(O)—, —O—, —S—, or —S(O)—, and R⁴ can be a halogen (e.g. F) or a methyl group.

In another aspect, the present teachings provide methods for preparing compounds of formula II:

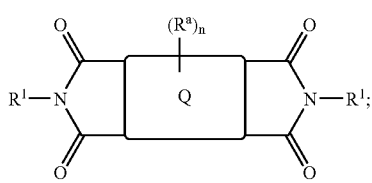

the methods can include reacting a compound having formula Ia:

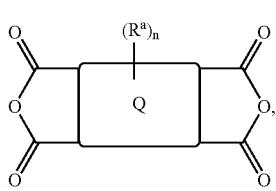

with an amine of the formula R¹NH₂, or reacting a compound having formula Ib:

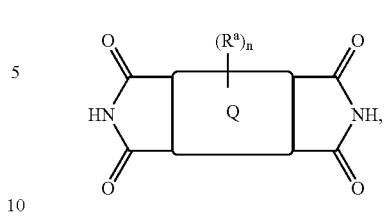

with a compound having the formula R¹-LG, wherein LG is a leaving group and Q, $R^a$, R¹, and n are as defined above.

In some embodiments, LG can be selected from Cl, Br, I, N₃, OTs, OMs, NO₂, SCN, and CN.

In various embodiments, compound of formula Ib can be prepared by reacting compounds of formula Ia with a nitrogen source. For example, the nitrogen source can be NH₃.

In various embodiments, compounds of formula Ia can be prepared by reacting compounds of formula III:

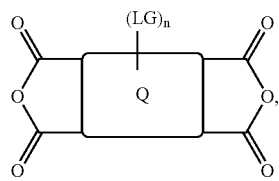

with a cyanide;
wherein LG is a leaving group; and
n is as defined herein.

In certain embodiments, LG can be selected from halide, N₃, —OTs, —OMs, —ONs, —OBs, and —OTf. In particular embodiments, LG can be Br.

In certain embodiments, the cyanide can be LiCN, NaCN, KCN, CuCN, AgCN, or trimethylsilyl cyanide (TMSCN). For example, the cyanide can be CuCN or AgCN. In particular embodiments, the cyanide can be CuCN.

Compounds of the present teachings can be prepared in accordance with the procedures outlined in Scheme 1 below, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., ¹H or ¹³C), infrared spectroscopy (IR), spectrophotometry (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

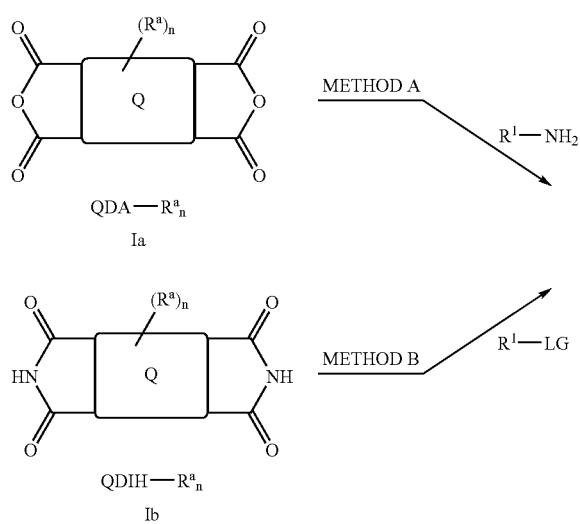

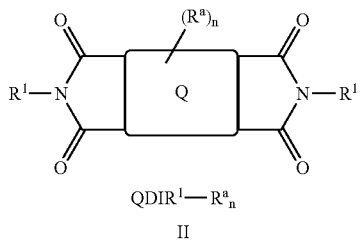

As shown in Scheme 1, in some embodiments, a compound of formula II can be prepared by reacting a compound of formula Ia with an amine of formula $R^1NH_2$. In other embodiments, a compound of formula II can be prepared by reacting a compound of formula Ib with a compound of formula $R^1$-LG, where LG is a leaving group as defined herein. For example, LG can be selected from Cl, Br, I, $N_3$, —SCN, OTs, OMs, $NO_2$, and CN.

In some embodiments, compounds of formula Ia or Ib can be reacted with $R^1NH_2$ or $R^1$-LG, respectively, in a co-solvent system. In certain embodiments, the co-solvent system can include a polar solvent and a low-polarity/non-polar solvent. For example, the polar solvent can be a protic solvent. In particular embodiments, the co-solvent system can include xylene and propanoic acid.

Compounds of the present teachings include, but are not limited to, the compounds presented in Table 1 and Table 2.

TABLE 1

| Cpd # | Name | Structure |
|---|---|---|
| 1 | 1,7-Dicyanoperylene-3,4:9,10-dianhydride (PDA-CN$_2$) | 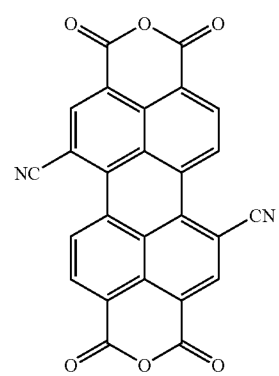 |
| 2 | 2,6-Dicyanonapthalene-1,4:5,8-dianhydride (NDA-CN$_2$) | 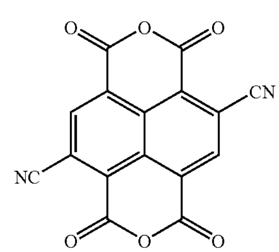 |

TABLE 1-continued
| Cpd # | Name | Structure |
|---|---|---|
| 3 | 9,10-Dicyanoanthracene-2,3:6,7-dianhydride (ADA-CN$_2$) | 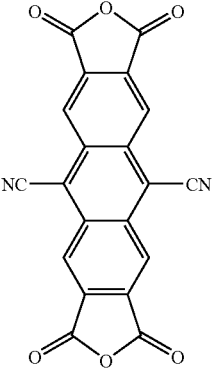 |
| 4 | 1,7-Dicyanoperylene-3,4:9,10-bis(dicarboximide) (PDIH-CN$_2$) | 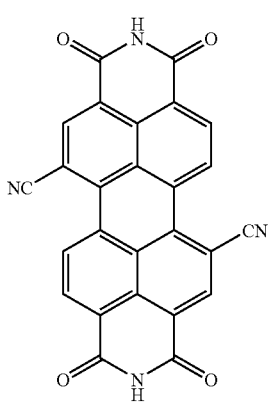 |
| 14 | N,N'-dioctyl-2,6-dicyanonapthalene-1,4:5,8-bis(dicarboximide) (NDI8-CN2) | 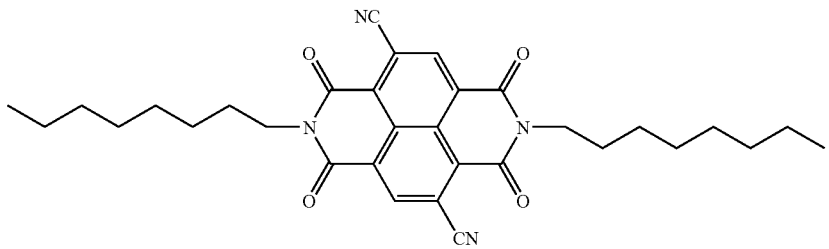 |
| 15 | N,N'-{4-[(3S)-3,7-dimethyl-6-octenyl]phenyl}-2,6-dicyanonapthalene-1,4:5,8-bis(dicarboximide) (PDICytr-CN2) | 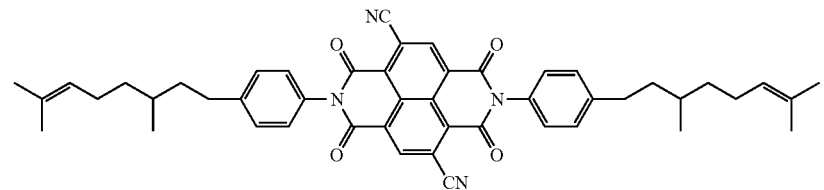 |
| 16 | N,N'-dioctyl-9,10-dicyanoanthracene-2,3:6,7-bis(dicarboximide) (ADI8-CN2) | 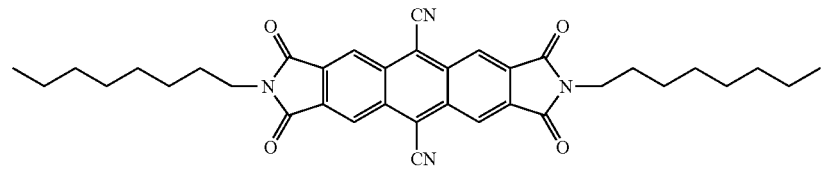 |

TABLE 2

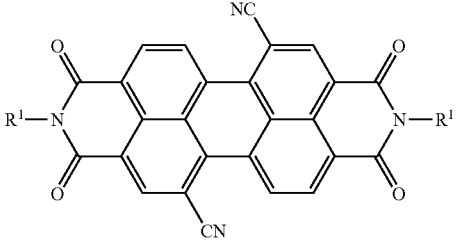

| Cpd # | Name | R¹ |
|---|---|---|
| 5a | N,N'-bis[n-octyl]-1,7-dicyanoperylene-3,4:9,10-bis(dicarboximide) (PDI8-CN$_2$) | 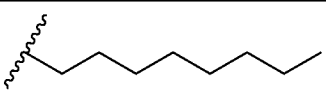 |
| 5b | N,N'-bis[n-octyl]-1,7-dicyanoperylene-3,4:9,10-bis(dicarboximide) (PDI8-CN$_2$) | 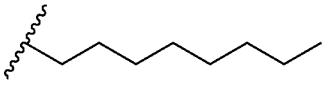 |
| 6 | N,N'-bis[(3S)-3,7-dimethyocten-6-yl]-1,7-dicyanoperylene-3,4:9,10-bis(dicarboximide) (PDICytr-CN$_2$) | 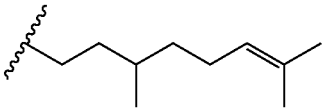 |
| 7a | N,N'-bis[(3S)-3,7-dimethyloctyl]-1,7-dicyanoperylene-3,4:9,10-bis(dicarboximide) (PDIRCytr-CN$_2$) | 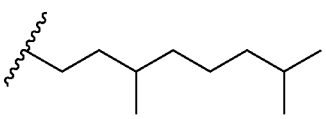 |
| 7b | N,N'-bis[(3S)-3,7-dimethyloctyl]-1,7-dicyanoperylene-3,4:9,10-bis(dicarboximide) (PDIRCytr-CN$_2$) | 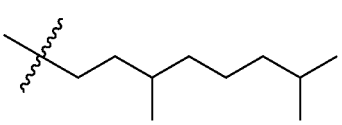 |
| 7c | N,N'-bis[2-ethylhexyl]-1,7-dicyanoperylene-3,4:9,10-bis(dicarboximide) (PDI2EH-CN$_2$) | 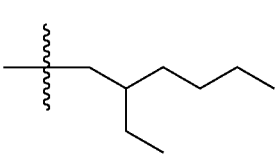 |
| 8 | N,N'-bis(4-n-hexylphenyl)-1,7-dicyanoperylene-3,4:9,10-bis(dicarboximide) (PDIPh6-CN$_2$) | 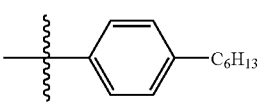 |
| 9 | N,N'-bis(4-picolyl)-1,7-dicyanoperylene-3,4:9,10-bis(dicarboximide) (PDI1Py-CN$_2$) | 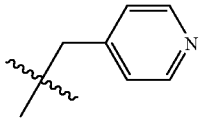 |
| 10 | N,N'-bis(6-tert-butyloxycarbonylaminohexyl)-1,7-dicyanoperylene-3,4:9,10-bis(dicarboximide) (PDI6NHBoc-CN$_2$) | 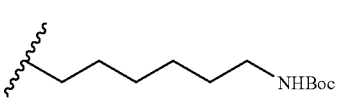 |
| 11 | N,N'-bis(9-anthracenyl)-1,7-dicyanoperylene-3,4:9,10-bis(dicarboximide) (PDI0A-CN$_2$) | 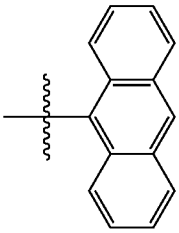 |

TABLE 2-continued

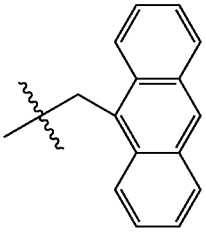

| Cpd # | Name | R¹ |
|---|---|---|
| 12 | N,N'-bis(anthracen-9-ylmethyl)-1,7-dicyanoperylene-3,4:9,10-bis(dicarboximide) (PDI1A-CN$_2$) | |
| 13 | N,N'-bis(2-(anthracen-9-yl)-ethyl)-1,7-dicyanoperylene-3,4:9,10-bis(dicarboximide) (PDI2A-CN$_2$) | |

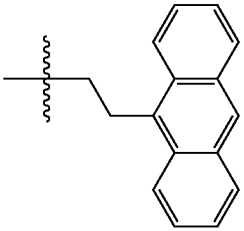

Compounds of formula II as well as compound of formulae Ia and Ib can be used to fabricate semiconducting materials and related electrical devices such as thin film semiconductors, field-effect devices, organic light-emitting diodes (OLEDs), organic photovoltaics, capacitors, and sensors. In some embodiments, compounds of formula I and II can have satisfactory solubilities in common solvents (e.g., water and common organic solvents), which can help to reduce manufacturing costs and offer processing advantages in the fabrication of these devices.

The following examples are provided to illustrate further and to facilitate the understanding of the present teachings and are not in any way intended to limit the invention.

Unless otherwise noted, all reagents were purchased from commercial sources and used without further purification. Some reagents were synthesized according to known procedures. Anhydrous tetrahydrofuran (THF) was distilled from sodium/benzophenone. Reactions were carried out under nitrogen unless otherwise noted. UV-vis spectra were recorded on a Cary Model 1 UV-vis spectrophotometer. NMR spectra were recorded on a Varian Unity Plus 500 spectrometer ($^1$H, 500 MHz; $^{13}$C, 125 MHz). Electrospray mass spectrometry was performed on a Thermo Finnegan model LCQ Advantage mass spectrometer.

EXAMPLE 1

Preparation of 1,7-dicyanoperylene-3,4:9,10-dianhydride

Figure 3:
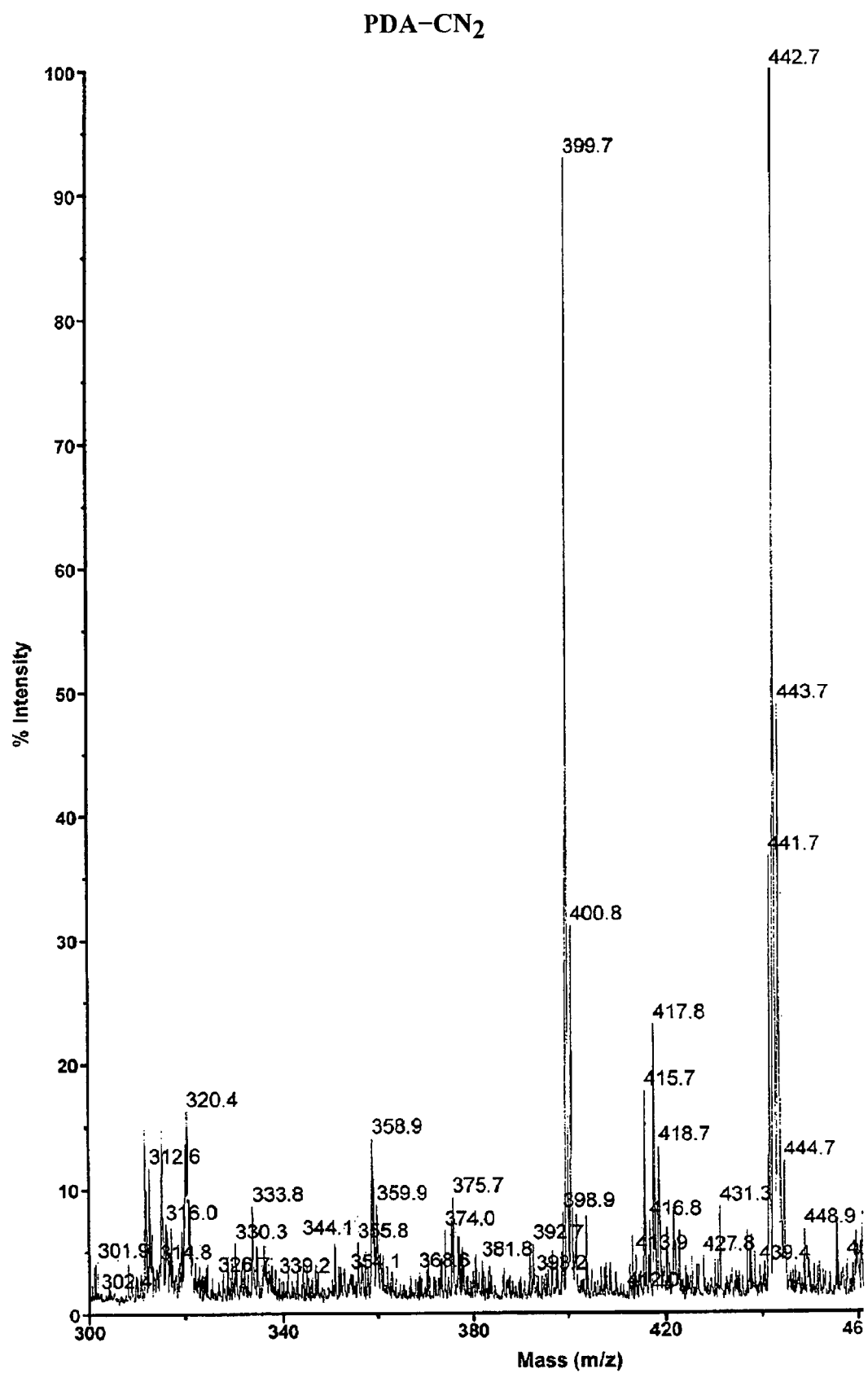
FIG. 3 provides the MS MALDI (Mass Spectroscopy/Matrix-assisted Laser Desorption/Ionization) spectrum of a compound of the present teachings (PDA-CN$_2$).

A mixture of 1,7-dibromoperylene-3,4:9,10-dianhydride (1.5 g, 2.73 mmol) and copper (I) cyanide (CuCN, 4.43 g, 49.5 mmol) in dimethylformamide (DMF, 70 mL) was deaerated and was heated at 150° C. for 6.5 hours. After cooling to room temperature, the precipitate was collected by filtration, washed with methanol, and dried overnight. The crude product was washed with an aqueous solution of potassium cyanide (KCN, 100 mmol) and with hot water to afford the product as a red solid (65% yield). MS-MALDI (Calcd 442.34): 442.7 (FIG. 3). M.p. >300° C.

EXAMPLE 2

Preparation of 2,6-dicyanonapthalene-1,4:5,8-dianhydride

Figure 4:
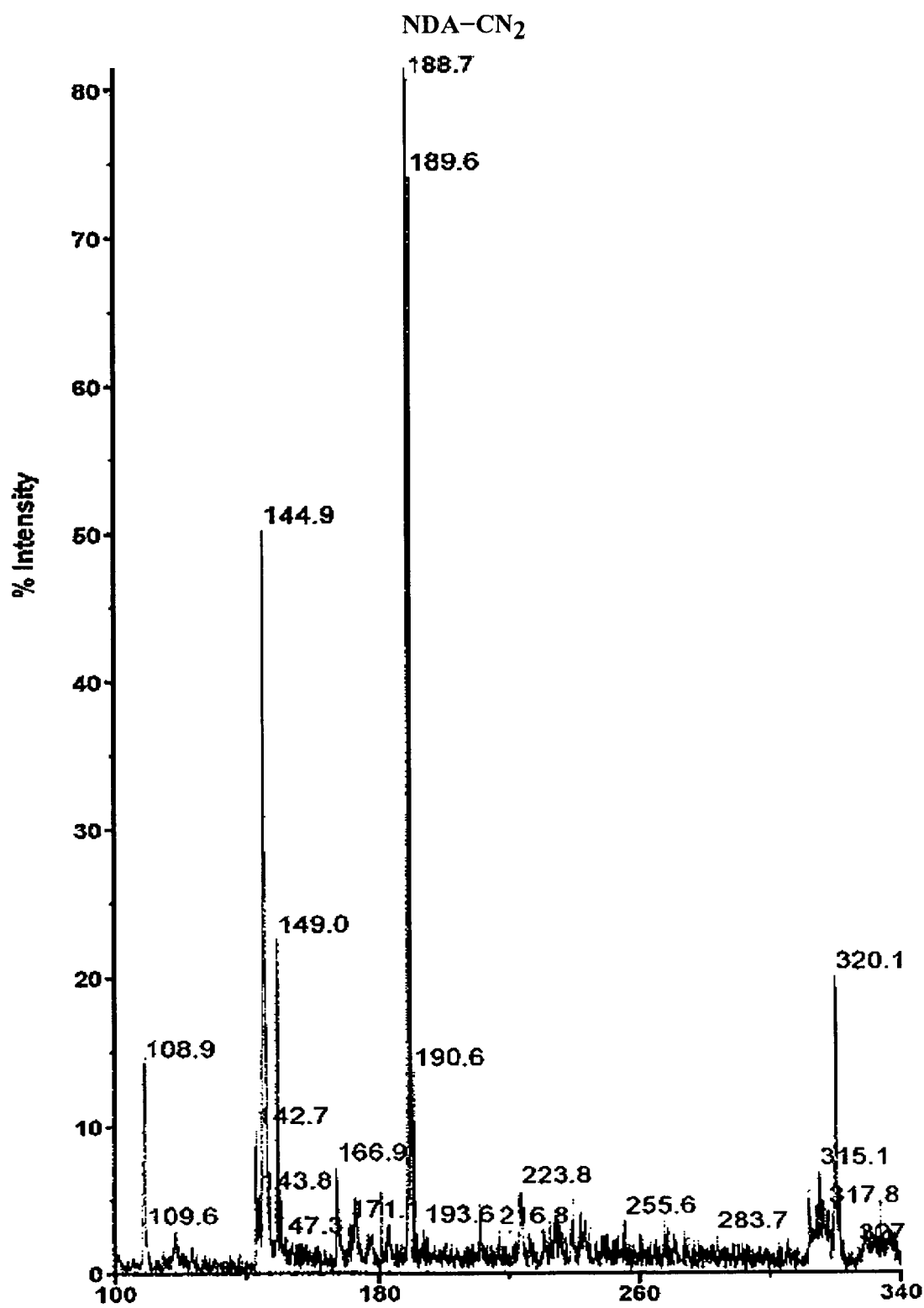
FIG. 4 provides the MS MALDI spectrum of a compound of the present teachings (NDA-CN$_2$).

A mixture of 2,6-dibromonapthalene-1,4:5,8-dianhydride (0.58 g, 1.40 mmol) and CuCN (2.22 g, 25.0 mmol) in DMF (25 mL) was deaerated and was heated at 150° C. for 4 hours. After cooling to room temperature, the precipitate was collected by filtration, washed with methanol, and dried overnight. The crude product was washed with an aqueous solution of KCN (50 mmol) and with hot water to afford the product as a light yellow solid (58% yield). MS-MALDI (Calcd 317.99) 318.1 (FIG. 4). M.p. >300° C.

EXAMPLE 3

Preparation of 9,10-dicyanoanthracene-2,3:6,7-dianhydride

A mixture of 2,6-dibromonapthalene-1,4:5,8-dianhydride (0.67 g, 1.40 mmol) and CuCN (2.22 g, 25.0 mmol) in DMF (30 mL) was deaerated and was heated at 150° C. for 5 hours. After cooling to room temperature, the precipitate was collected by filtration, washed with methanol, and dried overnight. The crude product was washed with an aqueous solution of KCN (50 mmol) and with hot water to afford the product as a light yellow solid (44.1% yield). MS-MALDI Calcd 368.01 found 369.0. M.p. >300° C.

EXAMPLE 4

Preparation of 1,7-dicyanoperylene-3,4:9,10-bis(dicarboximide)

Figure 5:
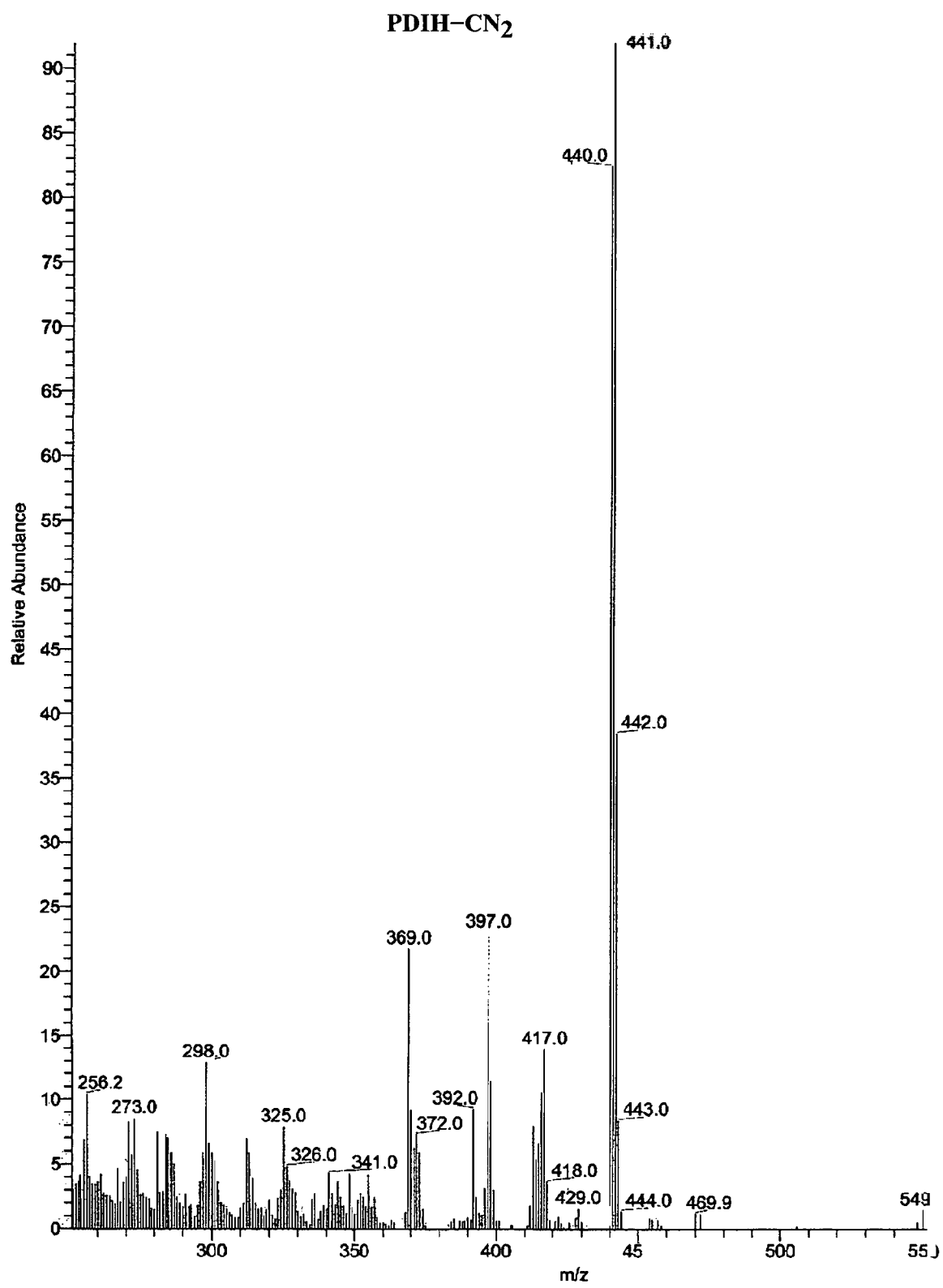
FIG. 5 provides the MS MALDI spectrum of a compound of the present teachings (PDIH-CN$_2$).

A mixture of ammonium acetate (3.62 g, 47.03 mmol) and 1,7-dicyanoperylene-3,4:9,10-dianhydride (100 mg, 0.226 mmol) in propanoic acid (25 mL) was heated at 145° C. for 1 hour. After cooling to room temperature, the precipitate was collected by filtration, washed with water and MeOH, and dried overnight (79% yield). MS-MALDI (Calcd 440.37) 440.9 (FIG. 5). EI-MS: found 441.0. M.p. >300° C.

EXAMPLE 5a

Preparation of N,N'-bis(n-octyl)-1,7-dicyanoperylene-3,4:9,10-bis(dicarboximide)

Method A n-Octylamine (117 mg, 0.9 mmol) was added to a mixture of 1,7-dicyanoperylene-3,4:9,10-dianhydride (200 mg, 0.45 mmol) in xylene (3 mL) and propanoic acid (0.7 mL). The reaction mixture was stirred at 145° C. for 5 minutes. After cooling to room temperature, MeOH (8 mL) was added and a precipitate formed, which was collected by filtration, washed with MeOH, and dried overnight. The product was obtained as a dark red solid (218 mg, 73% yield). $^1$H NMR (CHCl$_3$, 500 MHz): δ 9.71 (d, 2H), 8.99 (s, 2H), 8.94 (d, 2H), 4.23 (t, 4H), 1.77 (m, 4H), 1.56-1.3 (m, 20H), 0.90 (t, 6H). M.p. >300° C.

EXAMPLE 5b

Preparation of N,N'-bis(n-octyl)-1,7-dicyanoperylene-3,4:9,10-bis(dicarboximide)

(Method B). t-BuOH (3.6 mmol) was added to a suspension of 1,7-dicyanoperylene-3,4:9,10-bis(dicarboximide) (200 mg, 0.45 mmol) in dry DMF (10 mL). After stirring at room temperature for 6 hours, 1-bromooctane (468 mg, 3.6 mmol) was added and the reaction mixture was stirred for 16 hours. MeOH was added (40 mL) and the precipitate collected by filtration and washed with water and MeOH to afford the product as a red solid (38% yield).

EXAMPLE 6

Preparation of N,N'-bis[(3S)-3,7-dimethyloctan-6-yl]-1,7-dicyanoperylene-3,4:9,10-bis(dicarboximide)

Method A

Figure 8:
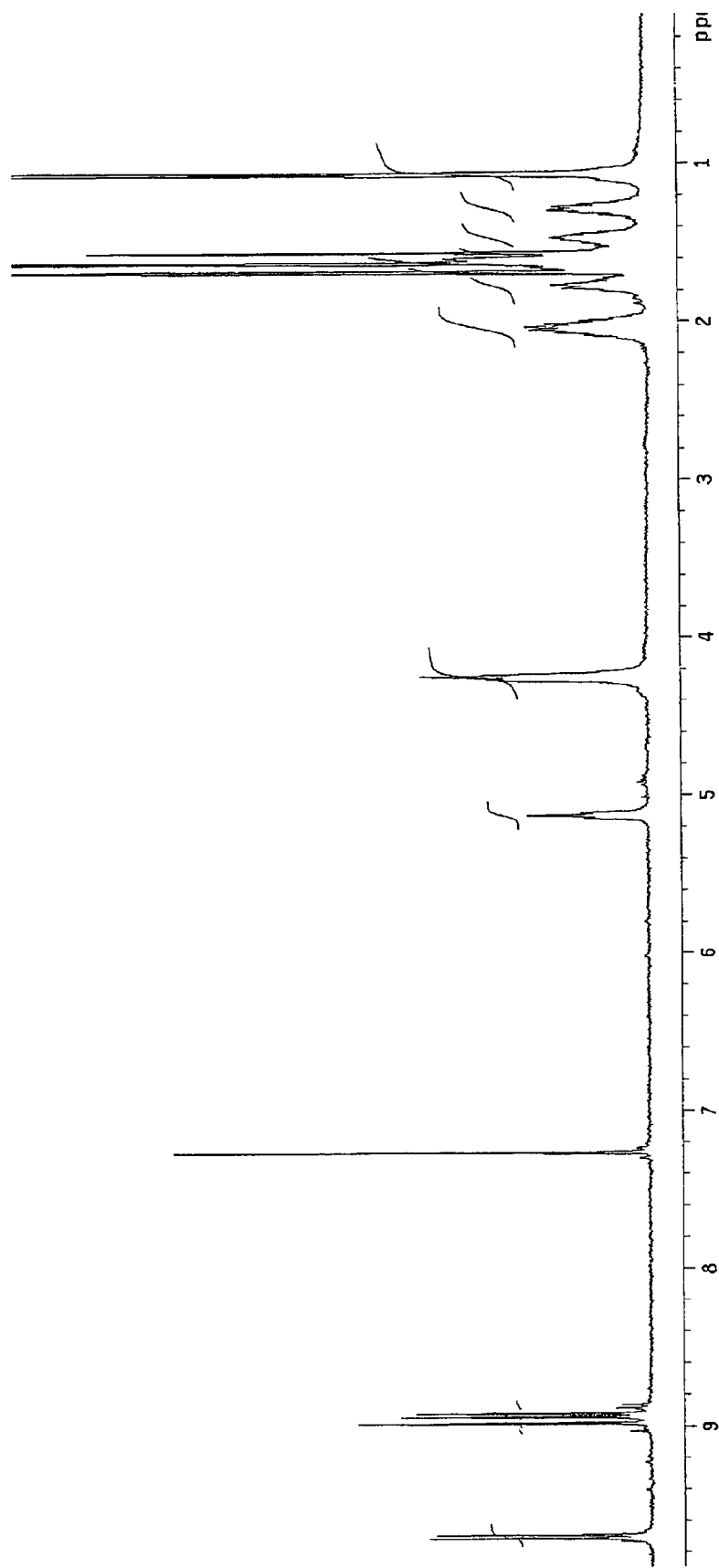
FIG. 8 provides the $^1$H NMR spectrum of a compound of the present teachings (PDICytr-CN$_2$) in CDCl$_3$.

Citronellylamine (5.00 g, 31.8 mmol) was added to a mixture of 1,7-dicyanoperylene-3,4:9,10-dianhydride (7.07 g, 15.9 mmol) in xylene (45 mL) and propanoic acid (10.5 mL). The reaction mixture was stirred at 145° C. for 10 minutes. After cooling to room temperature, MeOH (160 mL) was added and the precipitate was collected by filtration, washed with MeOH, and dried overnight to provide the product as a dark red solid (74% yield). M.p.=278° C. (DMF). EA: Calcd. for $C_{46}H_{44}N_4O_4$: C, 77.07; H, 6.19; N, 7.82; found C, 77.39; H, 6.18; N, 7.99; $^1$H NMR refers to FIG. 8.

EXAMPLE 7a

Preparation of N,N'-bis[(3S)-3,7-dimethyloctyl]-1,7-dicyanoperylene-3,4:9,10-bis(dicarboximide)

Figure 9:
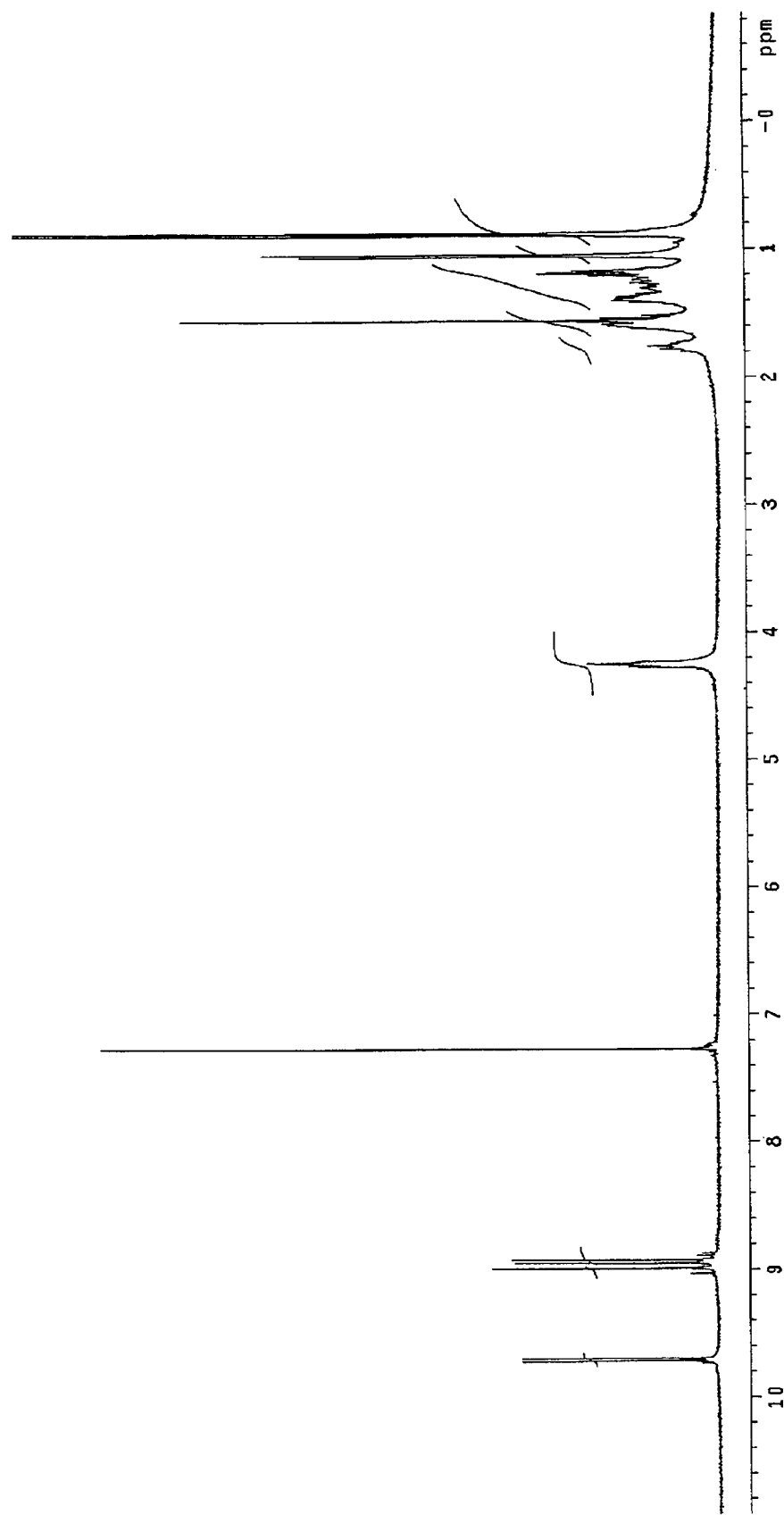
FIG. 9 provides the $^1$H NMR spectrum of a compound of the present teachings (PDIRCytr-CN$_2$) in CDCl$_3$.

Method A (3S)-3,7-Dimethyloctylamine (2.37 g, 15.0 mmol) was added to a mixture of 1,7-dicyanoperylene-3,4:9,10-dianhydride (3.00 mg, 7.54 mmol) in xylene (20 mL) and propanoic acid (5 mL). The reaction mixture was stirred at 145° C. for 10 minutes. After cooling to room temperature, MeOH (160 mL) was added and a precipitate, which was collected by filtration, washed with MeOH, and dried overnight. The product was obtained as a dark red solid (79% yield). EA: calc. C, 76.64; H, 6.71; N, 7.77; found C, 76.72; H, 6.86; N, 7.59; $^1$H NMR refers to FIG. 9.

EXAMPLE 7b

Preparation of N,N'-bis[(3S)-3,7-dimethyloctyl]-1,7-dicyanoperylene-3,4:9,10-bis(dicarboximide)

(Method B). t-BuOH (3.6 mmol) was added to a suspension of 1,7-dicyanoperylene-3,4:9,10-bis(dicarboximide) (200 mg, 0.45 mmol) in dry DMF (10 mL). After stirring at room temperature for 6 hours, citronellylbromide (3.6 mmol) was added and the reaction mixture was stirred for 16 hours. MeOH was added (50 mL) and the precipitate was collected by filtration and washed with water and MeOH to afford the product as a red solid (31% yield).

EXAMPLE 7c

Preparation of N,N'-bis(2-ethylhexyl)-1,7-dicyanoperylene-3,4:9,10-bis(dicarboximide)

Method A

Figure 10:
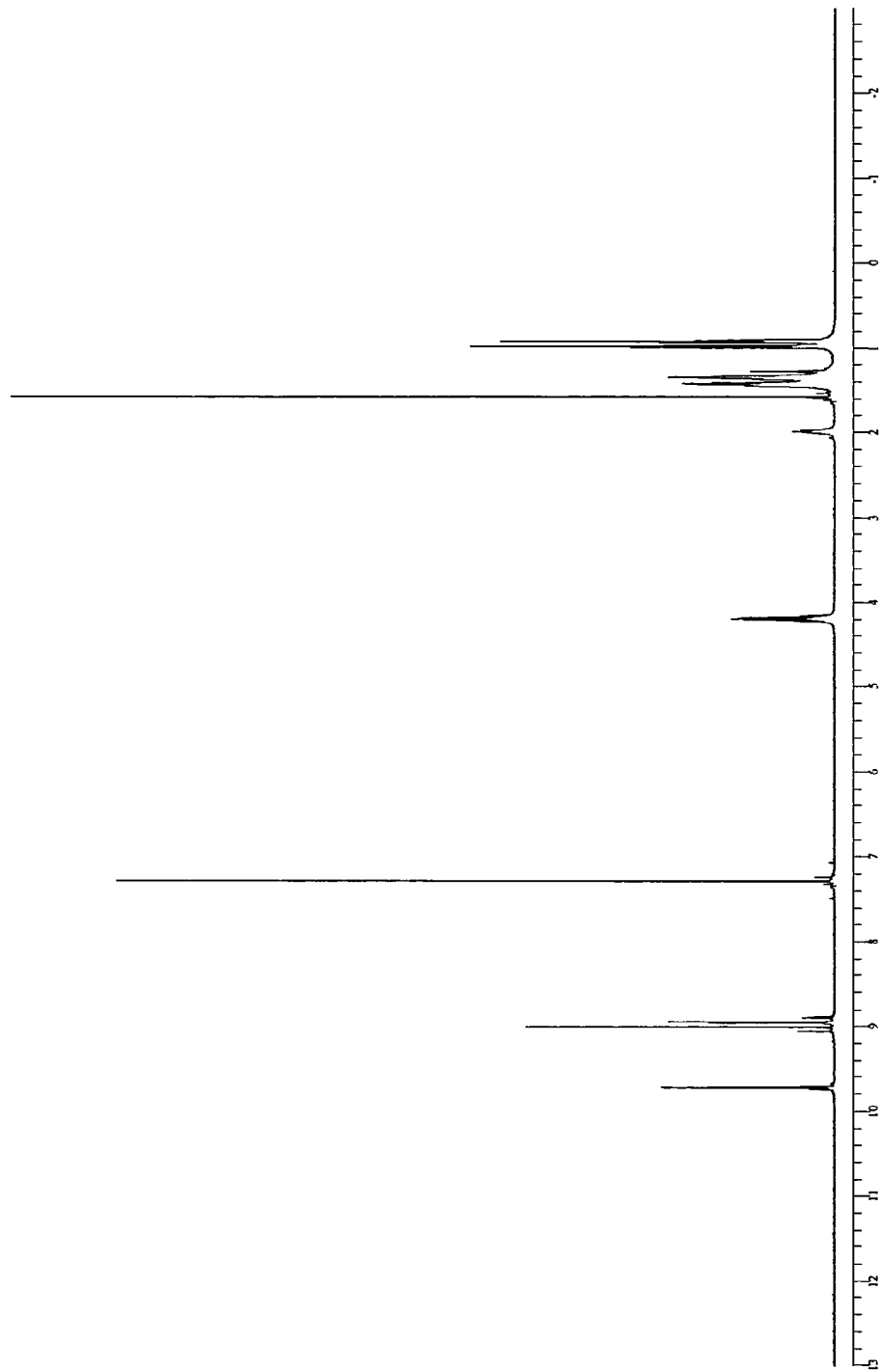
FIG. 10 provides the $^1$H NMR spectrum of a compound of the present teachings (PDI2EH-CN$_2$) in CDCl$_3$.

2-Ethylhexylamine (117 mg, 0.9 mmol) was added to a mixture of 1,7-dicyanoperylene-3,4:9,10-dianhydride (200 mg, 0.45 mmol) in xylene (3 mL) and propanoic acid (0.7 mL). The reaction mixture was stirred at 145° C. for 10 minutes. After cooling to room temperature, MeOH (10 mL) was added and a precipitate formed, which was collected by filtration, washed with MeOH, and dried overnight. The product was obtained as a dark red solid (198 mg, 66% yield). M.p. >319-321° C.; $^1$H NMR refers to FIG. 10.

EXAMPLE 8

Preparation of N,N'-bis(4-n-hexylphenyl)-1,7-dicyanoperylene-3,4:9,10-bis(dicarboximide)

Method A

A mixture of 4-hexylaniline (80.2 mg, 0.452 mmol) and 1,7-dicyanoperylene-3,4:9,10-dianhydride (100 mg, 0.226 mmol) in xylene (1.5 mL) and propanoic acid (0.34 mL) was heated at 145° C. for 5 minutes. After cooling to room temperature, MeOH (8 mL) was added and the precipitate was collected by filtration, washed with MeOH, and dried overnight. The product was obtained with a yield of 71%. $^1$H NMR (CHCl$_3$, 500 MHz): δ 9.77 (d, 2H), 9.04 (s, 2H), 9.00 (d, 2H), 7.42 (d, 4H), 7.26 (d, 4H), 2.73 (t, 4H), 1.72 (m, 4H), 1.55-1.35 (m, 12H), 0.93 (t, 6H). MS-MALDI Calcd 760.88 found 760.3. M.p. >300° C.

EXAMPLE 9

Preparation of N,N'-bis(4-picolyl)-1,7-dicyanoperylene-3,4:9,10-bis(dicarboximide)

Method A

Figure 7:
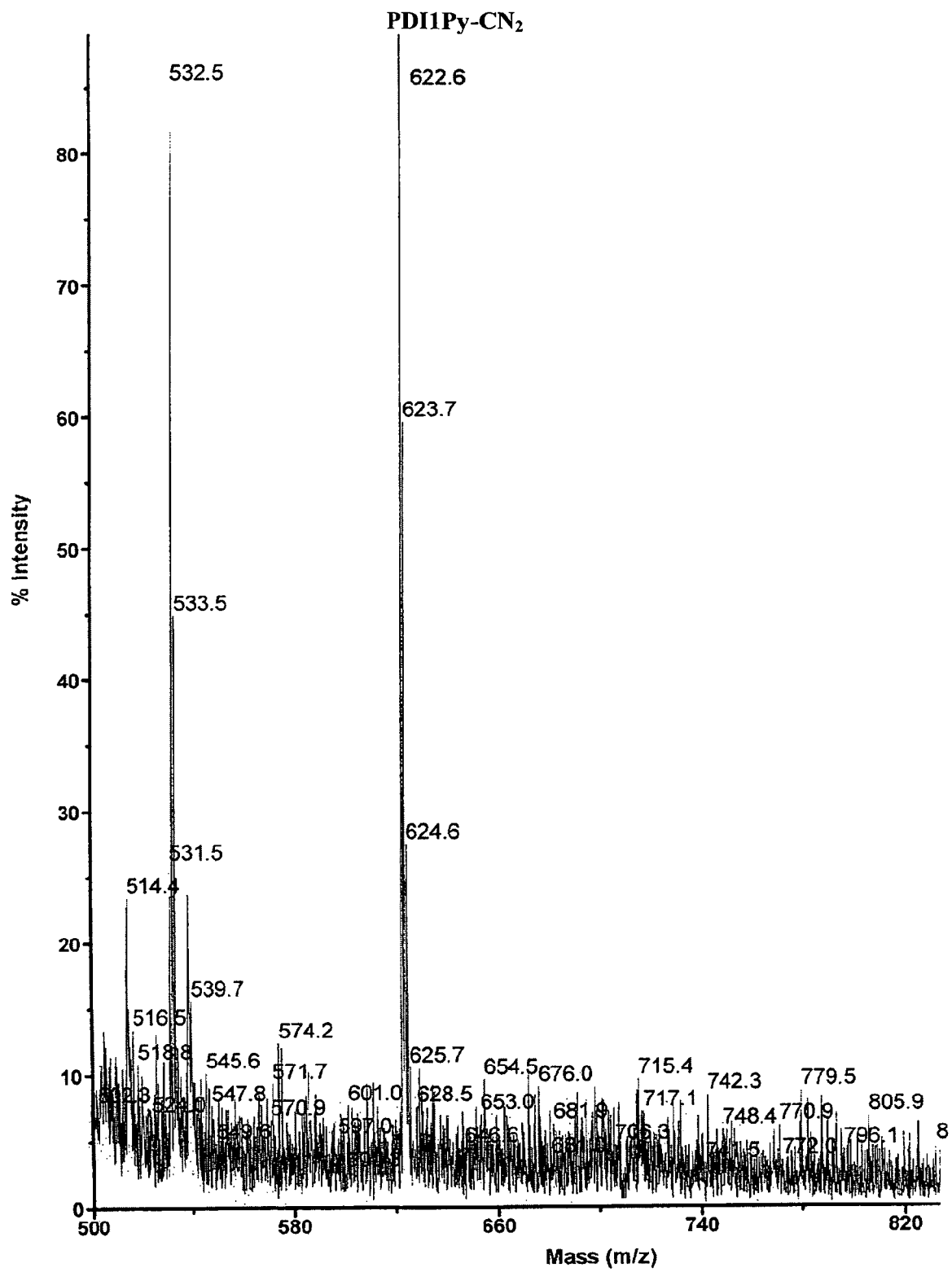
FIG. 7 provides the MS MALDI spectrum of a compound of the present teachings (PDI1Py-CN$_2$).

A mixture of 4-picolylamine (73 mg, 0.68 mmol) and 1,7-dicyanoperylene-3,4:9,10-dianhydride (150 mg, 0.34 mmol) in xylene (2.2 mL) and propanoic acid (0.5 mL) was heated at 145° C. for 5 minutes. After cooling to room temperature, MeOH (8 mL) was added and the precipitate was collected by filtration, washed with MeOH, and dried overnight. The product (171 mg) was obtained with a yield of 81%. MS-MALDI Calcd 622.59 found 622.6; M.p. >300° C.; $^1$H NMR refers to FIG. 7.

EXAMPLE 10

Preparation of N,N'-bis(6-tert-butyloxycarbonylaminohexyl)-1,7-dicyanoperylene-3,4:9,10-bis(dicarboximide)

Method A

Figure 6:
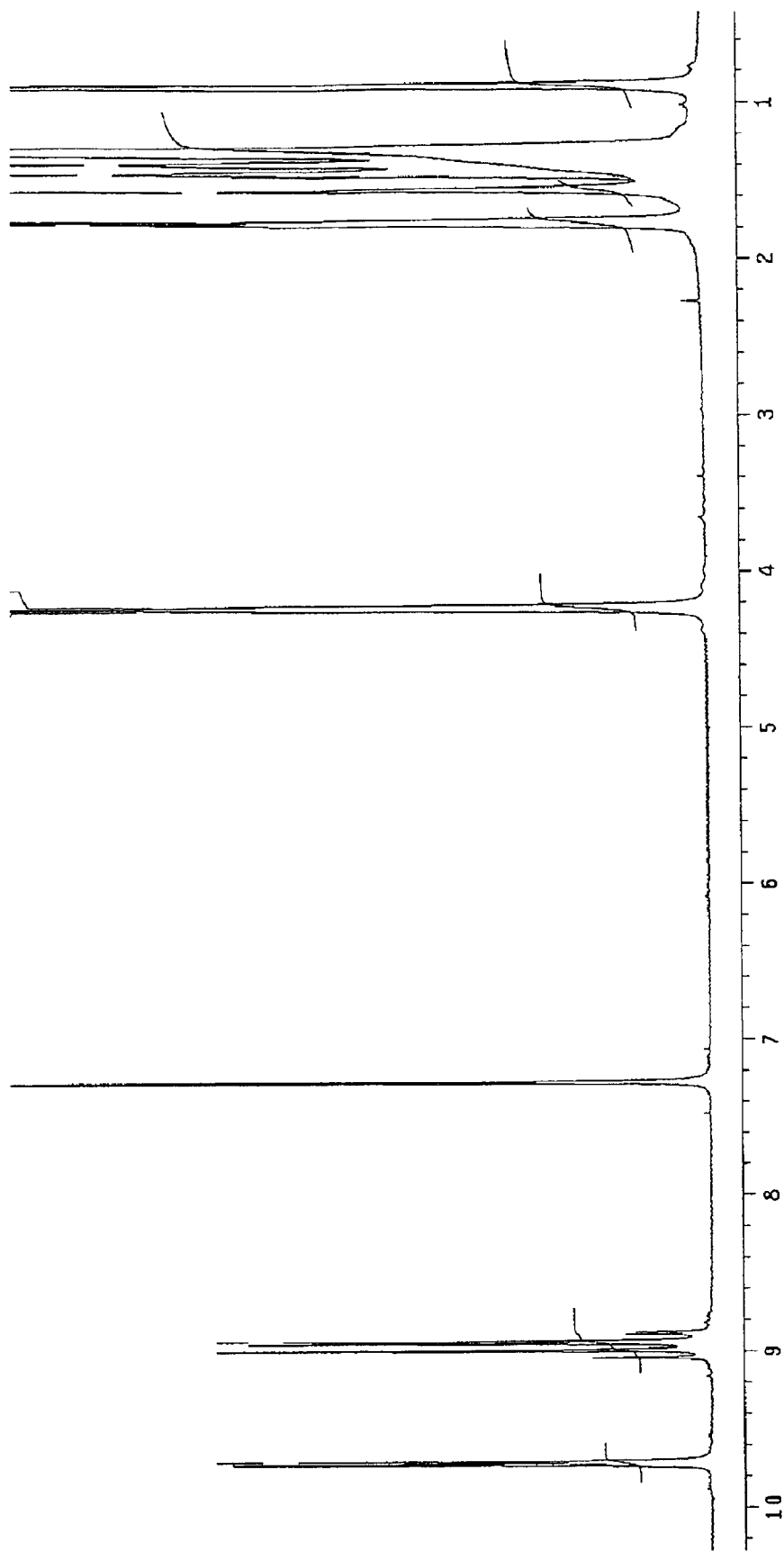
FIG. 6 provides the $^1$H NMR spectrum of a compound of the present teachings (PDI6NHBoc-CN$_2$) in CDCl$_3$.

A solution of N-butyloxycarbonyl-1,6-diaminohexane (N-BOC-1,6-diaminohexane, 1.73 g, 8 mmol) in 10 mL of xylene was added into a suspension of 1,7-dibromoperylene-3,4:9,10-dianhydride (2 g, 3.64 mmol) in xylene (30 mL) dropwise. The reaction mixture was stirred at 145° C. for 10 minutes. After cooling to room temperature, MeOH was added and the precipitate was collected by filtration, washed with MeOH, and dried overnight. The product was obtained with a yield of 66%. M.p. 210° C.; $^1$H NMR refers to FIG. 6.

EXAMPLE 11

Preparation of N,N'-bis(9-anthracenyl)-1,7-dicyanoperylene-3,4:9,10-bis(dicarboximide)

Method A

A mixture of 9-aminoanthracene (87.4 mg, 0.452 mmol) and 1,7-dicyanoperylene-3,4:9,10-dianhydride (100 mg, 0.226 mmol) in xylene (1.5 mL) and propanoic acid (0.34 mL) was heated at 145° C. for 8 minutes. After cooling to room temperature, MeOH (8 mL) was added and the precipitate was collected by filtration, washed with MeOH, and dried overnight. The product was obtained with a yield of 74%. M.p. >300° C.

EXAMPLE 12

Preparation of N,N'-bis(anthracene-9-ylmethyl)-1,7-dicyanoperylene-3,4:9,10-bis(dicarboximide)

A mixture of 9-methylaminoanthracene (93.7 mg, 0.452 mmol) and 1,7-dicyanoperylene-3,4:9,10-dianhydride (100 mg, 0.226 mmol) in xylene (1.5 mL) and propanoic acid (0.34 mL) was heated at 145° C. for 7 minutes. After cooling to room temperature, MeOH (8 mL) was added and the precipitate was collected by filtration, washed with MeOH, and dried overnight. The product was obtained with a yield of 64%. MS-MALDI Calcd 820.85 found 820.5. M.p. >300° C.

EXAMPLE 13

Preparation of N,N'-bis(2-(anthracene-9-yl)-ethyl)-1,7-dicyanoperylene-3,4:9,10-bis(dicarboximide)

Method A

A mixture of 9-(2-aminoethyl)anthracene (100 mg, 0.452 mmol) and 1,7-dicyanoperylene-3,4:9,10-dianhydride (100 mg, 0.226 mmol) in xylene (1.5 mL) and propanoic acid (0.34 mL) was heated at 145° C. for 5 minutes. After cooling to room temperature, MeOH (8 mL) was added and the precipitate was collected by filtration, washed with MeOH, and dried overnight. The product was obtained with a yield of 68%. M.p. >300° C.

EXAMPLE 14

Preparation of N,N'-dioctyl-2,6-dicyanonapthalene-1,4:5,8-bis(dicarboximide)

Method A n-Octylamine (0.42 mg, 3.2 mmol) was added to a mixture of 2,6-dicyanonapthalene-1,4:5,8-dianhydride (0.51 g, 1.6 mmol) in xylene (12 mL) and propanoic acid (2.8 mL). The reaction mixture was stirred at 145° C. for 8 minutes. After cooling to room temperature, MeOH (30 mL) was added and the precipitate was collected by filtration, washed with MeOH, and dried overnight. The product was obtained as a light yellow solid (69% yield).

EXAMPLE 15

Preparation of N,N'-{4-[(3S)-3,7-dimethyl-6-octenyl]phenyl}-2,6-dicyanonapthalene-1,4:5,8-bis(dicarboximide)

Method A

Citronellylamine (0.5 g, 3.2 mmol) was added to a mixture of 2,6-dicyanonapthalene-1,4:5,8-dianhydride (0.51 g, 1.6 mmol) in xylene (4.5 mL) and propanoic acid (1 mL). The reaction mixture was stirred at 145° C. for 10 minutes. After cooling to room temperature, MeOH (15 mL) was added and the precipitate was collected by filtration, washed with MeOH, and dried overnight. The product was obtained as a yellow solid (76% yield). $^1$H NMR (CDCl$_3$): δ 9.12 (s, 2H), 7.45 (d, 4H, J=8.1 Hz), 7.22 (d, 4H, J=8.1 Hz), 5.18 (t, 2H, J=7.1 Hz), 2.72 (t, 4H, J=7.8 Hz), 2.16-1.96 (m, 4H), 1.82-1.40 (m, 6H), 1.66 (s, 6H), 1.64 (s, 6H), 1.40-1.20 (m, 4H), 1.01 (d, 6H, J=6.6 Hz). EA Calcd. for C$_{48}$H$_{48}$N$_4$O$_4$: C, 77.39; H, 6.49; N, 7.52; found C, 77.81; H, 6.12; N, 7.09.

EXAMPLE 16

Preparation of N,N'-dioctyl-9,10-dicyanoanthracene-2,3:6,7-bis(dicarboximide)

Method A n-Octylamine (0.84 mg, 6.4 mmol) was added to a mixture of 9,10-dicyanoanthracene-2,3:6,7-dianhydride (1.2 g, 3.2 mmol) in xylene (23 mL) and propanoic acid (6 mL). The reaction mixture was stirred at 145° C. for 10 minutes. After cooling to room temperature, MeOH (60 mL) was added and a precipitate formed, which was collected by filtration, washed with MeOH, and finally dried overnight. The product was obtained as a light yellow solid (73% yield).

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

What is claimed is:

1. A compound of formula I:

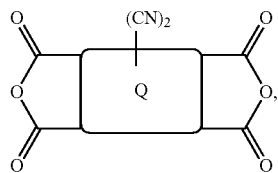

wherein Q is selected from a perylene moiety, a naphthalene moiety, an anthracene moiety, and a coronene moiety.

2. The compound of claim 1 selected from:

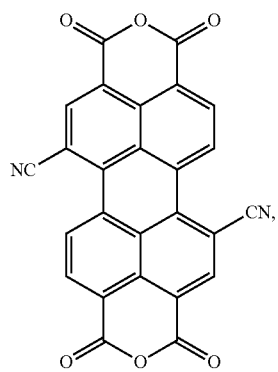

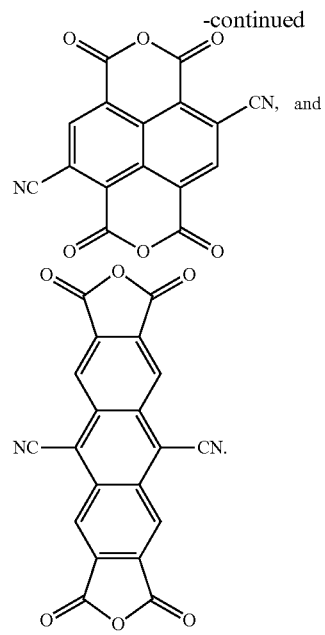

3. A method of using a compound of formula I according to claim 1 for preparing a compound of formula II:

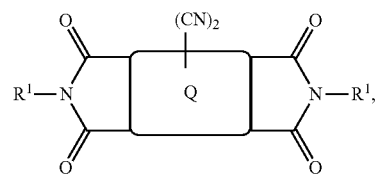

the method comprising reacting in a co-solvent system a compound of formula I

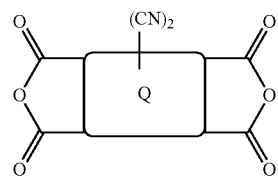

with an amine of the formula R$^1$NH$_2$, wherein:
  Q is selected from a perylene moiety, a naphthalene moiety, an anthracene moiety, and a coronene moiety; and
  R$^1$, at each occurrence, is -L-R$^2$ or -L-Ar$^1$—R$^2$,
    wherein:
    L, at each occurrence, is Y or (CH$_2$CH$_2$O)$_p$;
    Y, at each occurrence, is a divalent C$_{1-20}$ alkyl group, a divalent C$_{1-20}$ haloalkyl group, or a covalent bond;
    Ar$^1$ is a C$_{6-14}$ aryl group or a 5-14 membered heteroaryl group, each optionally substituted with 1-5 substituents independently selected from a halogen, —CN, a C$_{1-20}$ alkyl group, a C$_{2-20}$ alkenyl group, a C$_{1-20}$ alkoxy group, and a C$_{1-20}$ haloalkyl group;
    R$^2$, at each occurrence, is selected from a) —OR$^d$, b) —C(O)OR$^d$, c) —C(O)R$^e$, d) —C(O)NR$^e$R$^f$, e)

—C(S)OR$^d$, f) —C(S)R$^e$, g) —C(S)NR$^e$R$^f$, h) —SR$^d$, i) —S(O)$_2$OR$^d$, j) —S(O)$_2$R$^e$, k) —S(O)$_2$NR$^e$R$^f$, l) a C$_{1-20}$ alkyl group, m) a C$_{2-20}$ alkenyl group, n) a C$_{2-20}$ alkynyl group, o) a C$_{3-10}$ cycloalkyl group, p) a C$_{6-14}$ aryl group, q) a 3-12 membered cycloheteroalkyl group, and r) a 5-14 membered heteroaryl group, wherein each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-5-L-R$^3$ or -L-Ar$^2$—R$^3$ groups;

R$^d$, at each occurrence, is selected from a) H, b) —C(O)R$^e$, c) —C(O)NR$^e$R$^f$, d) —C(S)R$^e$, e) —C(S)NR$^e$R$^f$, f) a C$_{1-20}$ alkyl group, g) a C$_{2-20}$ alkenyl group, h) a C$_{2-20}$ alkynyl group, i) —Y—C$_{3-10}$ cycloalkyl group, j) —Y—C$_{6-14}$ aryl group, k) —Y-3-12 membered cycloheteroalkyl group, and l) —Y-5-14 membered heteroaryl group, wherein each of the C$_{1-20}$ alkyl group, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-5-L-R$^3$ groups;

R$^e$ and R$^f$, at each occurrence, independently are selected from a) H, b) —OH, c) —SH, d) —S(O)$_2$OH, e) —C(O)OH, f) —C(O)NH$_2$, g) —C(S)NH$_2$, h) —OC$_{1-20}$ alkyl, i) —O—Y—C$_{6-14}$ aryl, j) —C(O)—C$_{1-20}$ alkyl, k) —C(O)—OC$_{1-20}$ alkyl, l) 13 C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl)—Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl)—Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, and ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-5-L-R$^3$ groups;

Ar$^2$, at each occurrence, is a C$_{6-14}$ aryl group or a 5-14 membered heteroaryl group, each optionally substituted with 1-5 substituents independently selected from a halogen, —CN, a C$_{1-20}$ alkyl group, a C$_{2-20}$ alkenyl group, a C$_{1-20}$ haloalkyl group, and a C$_{1-20}$ alkoxy group;

R$^3$, at each occurrence, is selected from a) halogen, b) —CN, c) —NO$_2$, d) oxo, e) —OR$^g$, f) —SR$^g$, g) —NR$^g$R$^h$, h) —N(O)R$^g$R$^h$, i) —S(O)$_m$R$^g$, j) —S(O)$_m$OR$^g$, k) —S(O)$_m$NR$^g$R$^h$, l) —C(O)R$^g$, m) —C(O)OR$^g$, n) —C(O)NR$^g$R$^h$, o) —C(S)NR$^g$R$^h$, p) —SiH$_3$, q) —SiH(C$_{1-20}$ alkyl)$_2$, r) —SiH$_2$(C$_{1-20}$ alkyl), s) —Si(C$_{1-20}$ alkyl)$_3$, t) a C$_{1-20}$ alkyl group, u) a C$_{2-20}$ alkenyl group, v) a C$_{2-20}$ alkynyl group, w) a C$_{3-10}$ cycloalkyl group, x) a C$_{6-14}$ aryl group, y) a 3-12 membered cycloheteroalkyl group, or z) a 5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl group, the 3-12 membered cycloheteroalkyl group, and the 5-14 membered heteroaryl group optionally is substituted with 1-5-L-R$^4$ groups;

R$^g$ and R$^h$, at each occurrence, independently are selected from a) H, b) —OH, c) —SH, d) —S(O)$_2$OH, e) —C(O)OH, f) —C(O)NH$_2$, g) —C(S)NH$_2$, h) —OC$_{1-20}$ alkyl, i) —O—Y—C$_{6-14}$ aryl, j) —C(O)—C$_{1-20}$ alkyl, k) —C(O)—OC$_{1-20}$ alkyl, l) —C(S)N(C$_{1-20}$ alkyl)$_2$, m) —C(S)NH—C$_{1-20}$ alkyl, n) —C(O)NH—C$_{1-20}$ alkyl, o) —C(O)N(C$_{1-20}$ alkyl)$_2$, p) —S(O)$_m$—C$_{1-20}$ alkyl, q) —S(O)$_m$—OC$_{1-20}$ alkyl, r) —C(O)—Y—C$_{6-14}$ aryl, s) —C(O)—O—Y—C$_{6-14}$ aryl, t) —C(S)N(—Y—C$_{6-14}$ aryl)$_2$, u) —C(S)N(C$_{1-20}$ alkyl)—Y—C$_{6-14}$ aryl, v) —C(S)NH—Y—C$_{6-14}$ aryl, w) —C(O)NH—Y—C$_{6-14}$ aryl, x) —C(O)N(C$_{1-20}$ alkyl)—Y—C$_{6-14}$ aryl, y) —C(O)N(Y—C$_{6-14}$ aryl)$_2$, z) —S(O)$_m$—Y—C$_{6-14}$ aryl, aa) —S(O)$_m$—O—Y—C$_{6-14}$ aryl, ab) a C$_{1-20}$ alkyl group, ac) a C$_{2-20}$ alkenyl group, ad) a C$_{2-20}$ alkynyl group, ae) —Y—C$_{3-10}$ cycloalkyl group, af) —Y—C$_{6-14}$ aryl group, ag) —Y-3-12 membered cycloheteroalkyl group, and ah) —Y-5-14 membered heteroaryl group, wherein each of the C$_{1-20}$ alkyl groups, the C$_{2-20}$ alkenyl group, the C$_{2-20}$ alkynyl group, the C$_{3-10}$ cycloalkyl group, the C$_{6-14}$ aryl groups, the 3-12 membered cycloheteroalkyl group, and the 5-14 membered heteroaryl group optionally is substituted with 1-5-L-R$^4$ groups;

R$^4$, at each occurrence, is selected from a) halogen, b) —CN, c) —NO$_2$, d) oxo, e) —OH, f) —NH$_2$, g) —NH(C$_{1-20}$ alkyl), h) —N(C$_{1-20}$ alkyl)$_2$, i) —N(C$_{1-20}$ alkyl)—Y—C$_{6-14}$ aryl, j) —N(—Y—C$_{6-14}$ aryl)$_2$, k) —S(O)$_m$H, l) —S(O)$_m$C$_{1-20}$ alkyl, m) —S(O)$_2$OH, n) —S(O)$_m$—OC$_{1-20}$ alkyl, o) —S(O)$_m$—O—Y—C$_{6-14}$ aryl, p) —CHO, q) —C(O)—C$_{1-20}$ alkyl, r) —C(O)—C$_{6-14}$ aryl, s) —C(O)OH, t) —C(O)—OC$_{1-20}$ alkyl, u) —C(O)—O—Y—C$_{6-14}$ aryl, v) —C(O)NH$_2$, w) —C(O)NH—C$_{1-20}$ alkyl, x) —C(O)N(C$_{1-20}$ alkyl)$_2$, y) —C(O)NH—Y—C$_{6-14}$ aryl, z) —C(O)N(C$_{1-20}$ alkyl)—Y—C$_{6-14}$ aryl, aa) —C(O)N(—Y—C$_{6-14}$ aryl)$_2$, ab) —C(S)NH$_2$, ac) —C(S)NH—C$_{1-20}$ alkyl, ad) —C(S)N(C$_{1-20}$ alkyl)$_2$, ae) —C(S)N(—Y—C$_{6-14}$ aryl)$_2$, af) —C(S)N(C$_{1-20}$ alkyl)—Y—C$_{6-14}$ aryl, ag) —C(S)NH—Y—C$_{6-14}$ aryl, ah) —S(O)$_m$NH$_2$, ai) —S(O)$_m$NH(C$_{1-20}$ alkyl), aj) —S(O)$_m$N(C$_{1-20}$ alkyl)$_2$, ak) —S(O)$_m$NH(—Y—C$_{6-14}$ aryl), al) —S(O)$_m$N(C$_{1-20}$ alkyl)—Y—C$_{6-14}$ aryl, am) —S(O)$_m$N(—Y—C$_{6-14}$ aryl)$_2$, an) —SiH$_3$, ao) —SiH(C$_{1-20}$ alkyl)$_2$, ap) —SiH$_2$(C$_{1-20}$ alkyl), ar) —Si(C$_{1-20}$ alkyl)$_3$, as) a C$_{1-20}$ alkyl group, at) a C$_{2-20}$ alkenyl group, au) a C$_{2-20}$ alkynyl group, av) a C$_{1-20}$ alkoxy group, aw) a C$_{1-20}$ haloalkyl group, ax) a C$_{3-10}$ cycloalkyl group, ay) a C$_{6-14}$ aryl group, az) a 3-12 membered cycloheteroalkyl group, and ba) a 5-14 membered heteroaryl group;

m, at each occurrence, is 0, 1, or 2; and p, at each occurrence, is 0, 1, 2, 3, 4, 5, 6, 7, 8, 9, 10, 11, 12, 13, 14, 15, 16, 17, 18, 19, or 20.

4. The method of claim 3, wherein the compound of formula I is selected from:

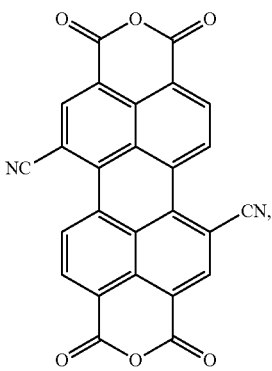

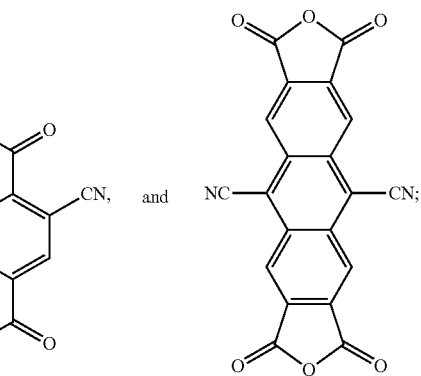

and the compound of formula II is selected from:

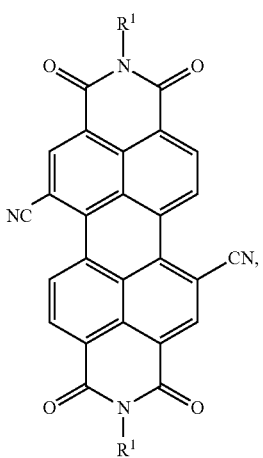

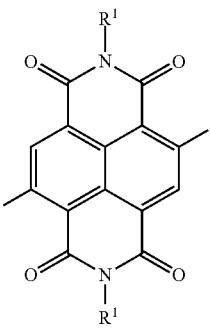

and

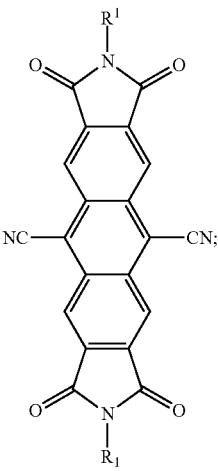

wherein $R^1$ is as defined in claim 3.

5. The method of claim 3, wherein $R^1$ is selected from a straight chain $C_{1-20}$ alkyl group, a branched $C_{1-20}$ alkyl group, a branched $C_{2-20}$ alkenyl group, a —Y—$C_{3-10}$ cycloalkyl group, a —Y—$C_{6-14}$ aryl group, a —Y-3-12 membered cycloheteroalkyl group, a —Y-5-14 membered heteroaryl group, wherein each of the $C_{1-20}$ alkyl groups, the $C_{2-20}$ alkenyl group, the $C_{3-10}$ cycloalkyl group, the $C_{6-14}$ aryl group, the 3-12 membered cycloheteroalkyl group, and the 5-14 membered heteroaryl group optionally is substituted with 1-5 -L-$R^3$ groups, and L and $R^3$ are as defined in claim 3.

6. The method of claim 3, wherein $R^1$ is selected from an n-octyl group, a (3S)-3,7-dimethyl-6-octenyl group, a (3S)-3,7-dimethyloctyl group, a 4-n-hexylphenyl group, a 4-picolyl group, a 6-tert-butyloxycarbonylaminohexyl group, a 9-anthracenyl group, an anthracen-9-ylmethyl group, and a 2-(anthracen-9-yl)-ethyl group.

7. The method of claim 3, wherein the compound of formula II is selected from:
N,N'-bis[n-octyl]-1,7-dicyanoperylene-3,4:9,10-bis(dicarboximide),
N,N'-bis[n-octyl]-1,6-dicyanoperylene-3,4:9,10-bis(dicarboximide),
N,N'-bis[(3S)-3,7-dimethyl-6-octenyl]-1,7-dicyanoperylene-3,4:9,10-bis(dicarboximide),
N,N'-bis[(3S)-3,7-dimethyl-6-octenyl]-1,6-dicyanoperylene-3,4:9,10-bis(dicarboximide),
N,N'-bis[(3S)-3,7-dimethyloctyl]-1,7-dicyanoperylene-3,4:9,10-bis(dicarboximide),
N,N'-bis[(3S)-3,7-dimethyloctyl]-1,6-dicyanoperylene-3,4:9,10-bis(dicarboximide),
N,N'-bis(2-ethylhexyl)-1,7-dicyanoperylene-3,4:9,10-bis(dicarboximide),
N,N'-bis(2-ethylhexyl)-1,6-dicyanoperylene-3,4:9,10-bis(dicarboximide),
N,N'-bis(4-n-hexylphenyl)-1,7-dicyanoperylene-3,4:9,10-bis(dicarboximide),
N,N'-bis(4-n-hexylphenyl)-1,6-dicyanoperylene-3,4:9,10-bis(dicarboximide),
N,N'-bis(4-picolyl)-1,7-dicyanoperylene-3,4:9,10-bis(dicarboximide),
N,N'-bis(4-picolyl)-1,6-dicyanoperylene-3,4:9,10-bis(dicarboximide),
N,N'-bis(6-tert-butyloxycarbonylaminohexyl)-1,7-dicyanoperylene-3,4:9,10-bis(dicarboximide), N,N'-bis(6-tert-butyloxycarbonylaminohexyl)-1,6-dicyanoperylene-3,4:9,10-bis(dicarboximide),
N,N'-bis(9-anthracenyl)-1,7-dicyanoperylene-3,4:9,10-bis(dicarboximide),
N,N'-bis(9-anthracenyl)-1,6-dicyanoperylene-3,4:9,10-bis(dicarboximide),
N,N'-bis(anthracen-9-ylmethyl)-1,7-dicyanoperylene-3,4:9,10-bis(dicarboximide),
N,N'-bis(anthracen-9-ylmethyl)-1,6-dicyanoperylene-3,4:9,10-bis(dicarboximide),
N,N'-bis(2-(anthracen-9-yl)-ethyl)-1,7-dicyanoperylene-3,4:9,10-bis(dicarboximide),
N,N'-bis(2-(anthracen-9-yl)-ethyl)-1,6-dicyanoperylene-3,4:9,10-bis(dicarboximide),
N,N'-dioctyl-2,6-dicyanonapthalene-1,4:5,8-bis(dicarboximide),
N,N'-{4-[(3S)-3,7-dimethyl-6-octenyl]phenyl}-2,6-dicyanonaphthalene-1,4:5,8-bis(dicarboximide), and
N,N'-dioctyl-9,10-dicyanoanthracene-2,3:6,7-bis(dicarboximide).

8. The method of claim 3, wherein $R^1$ is selected from an optionally substituted aryl group, an optionally substituted biaryl group, an optionally substituted arylalkyl group, and an optionally substituted biarylalkyl group.

9. The method of claim 3, wherein the co-solvent system comprises a first solvent and a second solvent, wherein the first solvent is a polar protic solvent and the second solvent is a non-polar solvent or an aprotic solvent.

10. The method of claim 3, wherein the co-solvent system comprises xylene and propanoic acid.

11. The method of claim 9, wherein the first solvent is propanoic acid.

12. The method of claim 9, wherein the second solvent is xylene.

13. The compound of claim 1, wherein Q is a perylene moiety.

14. The compound of claim 1, wherein Q is a naphthalene moiety.

15. The method of claim 3, wherein Q is a perylene moiety.

16. The method of claim 3, wherein Q is a naphthalene moiety.

17. The method of claim 3, wherein the compound of formula I is obtained by reacting a cyanide with a compound of formula III

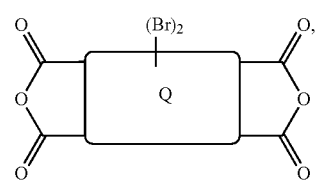

wherein Q is as defined in claim 3.

18. The method of claim 17, wherein the cyanide is selected from LiCN, NaCN, KCN, CuCN, AgCN, and trimethylsilyl cyanide.

19. A method for preparing a compound of formula I according to claim 1:

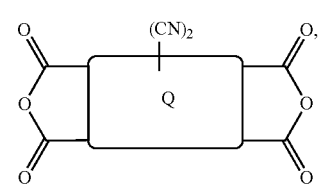

the method comprising reacting a cyanide with a compound of formula III

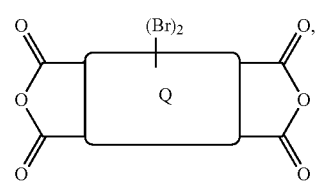

wherein Q is selected from a perylene moiety, a naphthalene moiety, an anthracene moiety, and a coronene moiety.

* * * * *